(12) United States Patent
McBride et al.

(10) Patent No.: US 11,134,994 B2
(45) Date of Patent: Oct. 5, 2021

(54) SPINAL-CORRECTION SYSTEM HAVING THREADED EXTENDER TABS AND REDUCTION TAB EXTENDERS

(71) Applicant: Warsaw Orthopedic, Inc., Warsaw, IN (US)

(72) Inventors: Larry McBride, Memphis, TN (US); Joseph H. Perra, Wayzata, MN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 16/776,546

(22) Filed: Jan. 30, 2020

(65) Prior Publication Data

US 2021/0236178 A1    Aug. 5, 2021

(51) Int. Cl.
*A61B 17/70*    (2006.01)

(52) U.S. Cl.
CPC ...... *A61B 17/7091* (2013.01); *A61B 17/7032* (2013.01)

(58) Field of Classification Search
CPC .............. A61B 17/708; A61B 17/7083–7091
See application file for complete search history.

(56) References Cited

U.S. PATENT DOCUMENTS

| | | | | |
|---|---|---|---|---|
| 7,462,182 B2* | 12/2008 | Lim | .................. | A61B 17/7086 606/99 |
| 7,491,208 B2* | 2/2009 | Pond, Jr. | ............ | A61B 17/7082 606/104 |
| 7,651,502 B2* | 1/2010 | Jackson | ............. | A61B 17/7091 606/99 |
| 7,887,539 B2* | 2/2011 | Dunbar, Jr. | ........ | A61B 17/7091 606/86 A |
| 7,918,857 B2* | 4/2011 | Dziedzic | ............ | A61B 17/7076 606/86 A |
| 7,931,673 B2* | 4/2011 | Hestad | ............... | A61B 17/7085 606/246 |
| 8,002,798 B2* | 8/2011 | Chin | .................. | A61B 17/3201 606/246 |
| 8,038,699 B2* | 10/2011 | Cohen | ................ | A61B 17/7076 606/246 |
| 8,066,739 B2* | 11/2011 | Jackson | ............... | A61B 17/702 606/246 |
| 8,096,996 B2* | 1/2012 | Gutierrez | ........... | A61B 17/7086 606/86 A |

(Continued)

*Primary Examiner* — Lynnsy M Summitt
(74) *Attorney, Agent, or Firm* — Fox Rothschild LLP

(57) ABSTRACT

A spinal-correction system having (i) a receiver including a base and opposing arms extending proximally from the base forming a rod-receiving cavity, (ii) a pair of extender tabs, each extender tab having threaded inner walls for receiving threads of a setscrew, (iii) a pair of tab extenders each being connectable releasably to one of the extender tabs, (iv) a cap instrument connectable releasably to the tab extenders, and (v) a pair of breakoff sections, each connecting one of the extender tabs to one of the receiver arms, and each being readily breakable for separating the extender tab from the receiver arm. The distal base defines a bonescrew cavity to receive a bonescrew head so that the head can move relative to the base. Each receiver arm has threaded inner walls for receiving setscrew threads. The rod-receiving cavity has geometry corresponds to geometry of the setscrew and a spinal-correction rod.

20 Claims, 17 Drawing Sheets

(56) References Cited

U.S. PATENT DOCUMENTS

| | | | | |
|---|---|---|---|---|
| 8,394,109 | B2 * | 3/2013 | Hutton | A61B 17/7086 606/105 |
| 8,439,924 | B1 * | 5/2013 | McBride | A61B 17/708 606/86 A |
| 8,469,960 | B2 * | 6/2013 | Hutton | A61B 17/7091 606/86 A |
| 8,496,661 | B2 * | 7/2013 | Moore | A61B 17/7085 606/86 A |
| 8,535,318 | B2 * | 9/2013 | Peterson | A61B 17/7082 606/86 A |
| 8,540,718 | B2 * | 9/2013 | Dauster | A61B 17/7086 606/86 A |
| 8,545,505 | B2 * | 10/2013 | Sandstrom | A61B 17/7086 606/86 A |
| 8,603,094 | B2 * | 12/2013 | Walker | A61B 17/86 606/86 A |
| 8,608,746 | B2 * | 12/2013 | Kolb | A61B 17/708 606/86 A |
| 8,617,218 | B2 * | 12/2013 | Justis | A61B 17/7085 606/278 |
| 8,795,283 | B2 * | 8/2014 | Petit | A61B 17/708 606/86 A |
| 8,894,655 | B2 * | 11/2014 | Fallin | A61B 17/7041 606/86 A |
| RE45,338 | E * | 1/2015 | Chin | A61B 17/7035 606/246 |
| 8,932,210 | B2 * | 1/2015 | Woods | A61B 17/7085 600/201 |
| 8,936,606 | B2 * | 1/2015 | Gleason | A61B 17/7088 606/104 |
| 9,198,692 | B1 * | 12/2015 | Doose | A61B 17/7086 |
| 9,220,539 | B2 * | 12/2015 | McBride | A61B 17/7086 |
| 9,289,250 | B2 * | 3/2016 | Wall | A61B 17/708 |
| 9,314,273 | B2 * | 4/2016 | Iott | A61F 2/4611 |
| 9,314,274 | B2 * | 4/2016 | Amstutz | A61B 17/7038 |
| 9,333,012 | B2 * | 5/2016 | Beale | A61B 17/7076 |
| 9,414,862 | B2 * | 8/2016 | Miller | A61B 17/7032 |
| 9,451,998 | B2 * | 9/2016 | McBride | A61B 17/7085 |
| 9,468,474 | B2 * | 10/2016 | Parikh | A61B 17/7086 |
| 9,510,874 | B2 * | 12/2016 | Kruger | A61B 17/7076 |
| 9,510,875 | B2 * | 12/2016 | Reitblat | A61B 17/7091 |
| 9,517,099 | B2 * | 12/2016 | Bess | A61B 17/7086 |
| 9,526,537 | B2 * | 12/2016 | Meyer | A61B 17/7086 |
| 9,532,814 | B2 * | 1/2017 | Harper | A61B 17/8886 |
| 9,561,062 | B2 * | 2/2017 | Hayes | A61B 17/025 |
| 9,622,795 | B2 * | 4/2017 | Reitblat | A61B 17/7079 |
| 9,629,667 | B2 * | 4/2017 | Petit | A61B 17/7091 |
| 9,655,653 | B2 * | 5/2017 | Lindner | A61B 17/7091 |
| 9,743,958 | B2 * | 8/2017 | Ishii | A61B 17/7032 |
| 9,743,962 | B2 * | 8/2017 | Viart | A61B 17/7086 |
| 9,750,545 | B2 * | 9/2017 | Cryder | A61B 17/7004 |
| 9,844,398 | B2 * | 12/2017 | Daniels | A61B 17/7086 |
| 9,844,400 | B2 * | 12/2017 | Stevenson | A61B 17/7082 |
| 9,907,582 | B1 * | 3/2018 | Olea | A61B 17/60 |
| 9,936,987 | B2 * | 4/2018 | Gnoth | A61B 17/7091 |
| 9,999,451 | B2 * | 6/2018 | Biedermann | A61B 17/7032 |
| 10,052,140 | B2 * | 8/2018 | Krause | A61B 17/7037 |
| 10,159,579 | B1 * | 12/2018 | Reitblat | A61B 17/70 |
| 10,631,901 | B2 * | 4/2020 | Fiechter | A61B 17/862 |
| 10,687,868 | B2 * | 6/2020 | Heuer | A61B 17/7076 |
| 10,702,317 | B2 * | 7/2020 | Kam | A61B 17/7032 |
| 10,709,489 | B2 * | 7/2020 | Heuer | A61B 17/7032 |
| RE48,376 | E * | 1/2021 | Chin | A61B 90/00 |
| 2010/0036434 | A1 * | 2/2010 | Ely | A61B 17/7091 606/305 |
| 2012/0109208 | A1 * | 5/2012 | Justis | A61B 17/7089 606/264 |
| 2015/0066042 | A1 * | 3/2015 | Cummins | A61B 17/7091 606/104 |
| 2015/0173809 | A1 * | 6/2015 | Bechtel | A61B 17/7089 606/265 |
| 2016/0045227 | A1 * | 2/2016 | Stad | A61B 17/708 606/266 |
| 2016/0106480 | A1 * | 4/2016 | Zhou | A61B 17/7002 606/86 A |
| 2017/0128101 | A1 * | 5/2017 | Patrinicola | A61B 17/7052 |
| 2018/0036037 | A1 * | 2/2018 | Abell | A61B 17/7083 |
| 2018/0132911 | A1 * | 5/2018 | Wu | A61B 17/7088 |
| 2018/0353213 | A1 * | 12/2018 | Biedermann | A61B 17/7032 |
| 2019/0000512 | A1 * | 1/2019 | Jackson | A61B 17/7035 |
| 2019/0059959 | A1 * | 2/2019 | Serra | A61B 17/7083 |
| 2019/0142470 | A1 * | 5/2019 | Kim | A61B 17/7007 606/246 |
| 2019/0262044 | A1 * | 8/2019 | Roth | A61B 17/80 |
| 2019/0274741 | A1 * | 9/2019 | Vazifehdan | A61B 17/7086 |
| 2019/0380750 | A1 * | 12/2019 | Morris | A61B 17/7086 |
| 2020/0030118 | A1 * | 1/2020 | Italiaie | A61B 17/7002 |
| 2020/0107865 | A1 * | 4/2020 | Lu | A61B 17/7085 |
| 2020/0305932 | A1 * | 10/2020 | Park | A61B 17/708 |
| 2020/0323652 | A1 * | 10/2020 | Italiaie | A61B 17/7085 |

* cited by examiner

SPINAL-CORRECTION SYSTEM HAVING THREADED EXTENDER TABS AND REDUCTION TAB EXTENDERS

FIELD

The present disclosure relates to surgical systems, generally, and, more particularly, to a spinal-correction system having capped tab extenders connectable to a screw assembly having threaded extender tabs connected frangibly to a threaded uni-axial or multi-axial rod receiver and bonescrew.

BACKGROUND

Surgical rods are used commonly in correcting spinal abnormalities. Pedicle-screw assemblies are often used to facilitate securement of one or more spinal rods relative to the spine. Pedicle-screw assemblies include a bonescrew attached to a rod-receiving receiver. The bonescrews are attached to patient vertebrae, and the receivers receive portions of the spinal rod.

The receivers of typical pedicle-screw assemblies are in some cases angularly positionable with respect to the bonescrew to facilitate select orientation of the spinal rod with respect to the vertebrae. With the bonescrews fixed to the vertebrae, a user can in connecting the rod to the receiver persuade the spine toward a desired shape.

Positioning the rod within every receiver can be challenging in some procedures. The maneuvering can be especially difficult in minimally invasive procedures in which visibility and space to move are even more limited than in standard open spinal surgeries.

Systems are needed to facilitate reduction of rods into receivers anchored to patient vertebrae.

SUMMARY

Systems and processes of the present disclosure relate generally to surgical systems and, more particularly, to spinal surgical systems having capped tab extenders connectable to a screw assembly having threaded extender tabs connected frangibly to a threaded uni-axial or multi-axial rod receiver and bonescrew. In a contemplated embodiment, the receiver and bonescrew may have a fixed format, whereby the receiver does not move with respect to the screw.

In one aspect, the present disclosure provides a spinal-correction system having (i) a receiver having a distal base and a pair of opposing arms extending proximally from the base and forming a rod-receiving cavity, (ii) a pair of extender tabs, each arm having threaded inner walls sized and shaped for receiving threads of the setscrew, (iii) a pair of tab extenders each being connectable releasably to one of the extender tabs, (iv) a cap instrument connectable releasably to a proximal end of the tab extenders, and (v) a pair of breakoff sections, each connecting one of the extender tabs to one of the receiver arms, and each being configured for being broken readily for separating the extender tab from the receiver arm in operation of the system.

The distal base of the receiver defines a bonescrew cavity sized and shaped to receive a head of a bonescrew so that the head can move relative to the base. Each receiver arm has threaded inner walls for receiving threads of a setscrew. And the rod-receiving cavity has a size and shape corresponding to size and shape of the setscrew and a size and shape of a spinal-correction rod to be secured in the cavity by the setscrew in operation of the system.

In some embodiments, a threadform of each inner wall of the extender tabs extends from a distal end of the extender tab proximally least about half of a height of the extender tab.

A threadform of each inner wall of the extender tabs extends in some cases from a distal end of the extender tab proximally at least about two thirds of a height of the extender tab.

Each extender tab can have a locking aperture, and each tab extender can have a locking protrusion for engagement with a corresponding one of the locking apertures to releasably engage the tab extender to the extender tab, in various embodiments. In some cases, each tab extender has a cantilever-spring locking component connected to a balance of the tab extender only at a distal end of the cantilever-spring locking component, and the locking protrusion is positioned at or adjacent a proximal end of the cantilever-spring locking component.

The cap instrument in various embodiments extends from a proximal end to a distal end and has inner walls extending from the proximal end to the distal end of the cap instrument, the inner walls defining (a) a central-guide channel extending between the proximal and distal ends of the instrument, and (b) a tab-extender channel on each side of the central-guide channel.

In some cases, the cap instrument has (I) an outer wall extending between the proximal and distal ends, and (II) opposing engagement openings in each of the tab-extender channels. Each of the engagement openings extend between the inner and outer walls of the cap instrument, and each of the tab extenders extends from a proximal end to a distal end having a forked tip having a pair of opposing prongs. At least one of each set of opposing prongs has a prong protrusion for, in use of the system, engaging with one of the engagement openings of the cap instrument.

Each of the prongs have one of the prong protrusions configured in various embodiments to act as a cantilever spring biasing the prong protrusion of the prong outward, away from the opposing prong of the forked tip, thus forcing the prong protrusion into the engagement opening of the cap instrument when the forked tip is inserted in the tab-extender channel of the cap instrument.

In various embodiments, each tab extender has an inner wall and an outer wall, each extending from a proximal end to a distal end, the inner wall at the distal end forming an extender-tab-receiving channel having a back wall, opposing side walls, and an internal shoulder wall extending from each side inner wall forming a generally u-shaped extender-tab-receiving channel.

The receiver can be configured in a uni-axial format such that the receiver can be moved only along a single plane with respect to the bonescrew, or a multi-axial format such that the receiver can be moved anywhere within a generally conical space with respect to the bonescrew. The receiver and bonescrew has, in a contemplated embodiment, a fixed format, whereby the receiver does not more with respect to the screw.

In another aspect, the disclosure provides a spinal-correction system having (A) a receiver having a distal base and two opposing arms extending proximally from the base and forming a rod-receiving cavity, (B) a pair of extender tabs, each arm having threaded inner walls sized and shaped for receiving threads of the setscrew, a threadform of each inner wall of the extender tabs extending from a distal end of the extender tab proximally at least about two thirds of a total height of the extender tab, and (C) a pair of breakoff sections, each connecting one of the extender tabs to one of the receiver arms, and each being configured for being broken readily for separating the extender tab from the receiver arm in operation of the system. The distal base of the receiver defines a bonescrew cavity sized and shaped to receive the head of a bonescrew so that the head can move relative to the base. Each receiver arm has threaded inner walls for receiving threads of a setscrew. And the rod-receiving cavity has a size and shape corresponding to size and shape of the setscrew and a size and shape of a spinal-correction rod to be secured in the cavity by the setscrew in operation of the system.

In yet another aspect, the disclosure provides a spinal-correction system having (i) a receiver having a distal base and a pair of opposing arms extending proximally from the base and forming a rod-receiving cavity, (ii) a pair of extender tabs, each arm having threaded inner walls sized and shaped for receiving threads of the setscrew, a threadform of each inner wall of the extender tabs extending from a distal end of the extender tab proximally at least about half of a total height of the extender tab, (iii) a pair of breakoff sections, each connecting one of the extender tabs to one of the receiver arms, and each being configured for being broken readily for separating the extender tab from the receiver arm in operation of the system, and (iv) a pair of tab extenders each being connectable releasably to one of the extender tabs. The distal base of the receiver defines a bonescrew cavity sized and shaped to receive the head of a bonescrew so that the head can move relative to the base. Each receiver arm has threaded inner walls for receiving threads of a setscrew. The rod-receiving cavity has a size and shape corresponding to size and shape of the setscrew and a size and shape of a spinal-correction rod to be secured in the cavity by the setscrew in operation of the system. Each extender tab has a locking aperture. And each tab extender has a locking protrusion for engagement with a corresponding one of the locking apertures to releasably engage the tab extender to the extender tab.

Details of various aspects of the disclosure are set forth in the accompanying drawings and description below. Other features, objects, and advantages of the technology will be apparent from the description, drawings, and claims.

DETAILED DESCRIPTION

Bonescrew assemblies are used to connect rods to a patient spine in spinal surgery. Assemblies can be (i) fixed, whereby there is no relative movement between the receiver and the bonescrew, (ii) multi-axial, whereby the receiver can be rotated to any desired angle within a cone of space with respect to the bonescrew, and (iii) uni-axial, whereby the receiver can be moved only along a single plane with respect to the bonescrew. While much of the present disclosure refers to uni-axial screw assemblies, structures and techniques described can be readily implemented with multi-axial or fixed screw assemblies.

The spinal-correction system of the present technology includes a screw assembly having extender tabs connected frangibly to a rod receiver of the assembly. The screw assembly is connectable with instrumentation including tab-extender and cap instruments. The tab extenders, in addition to being used for positioning and reducing the rods (lowering into the receiver), can be used to retract or hold back patient skin and other soft tissues in the surgical procedure. By this function, the system obviates or reduces the need for additional retracting instrumentation, such as surgical tissue retractors.

The spinal-correction system includes a cap instrument connectable to the tab extenders, forming a reduction tower, which can be used to facilitate rod reduction and securement into the screw-assembly receiver.

In various embodiments, the uni-axial screw implant has extender tabs connected to a base by a breakoff section. The base has set-screw threads, and the extender tabs may include a complimentary threadform, above the breakoff section, through which the set-screw is threaded down toward the base and against the rod.

The system can obviate need for additional external reduction instrumentation, though external reduction instrumentation can be used, as described further below. The system can also obviate need for external retraction instrumentation, as also described further below. Not using such external instruments has various advantages, such as savings by avoiding storage needs, shipping needs, space needs, and work for preparation and handling in the OR, and cost savings from these and other factors including cost of the external instruments.

Uni-axial screw implants can be used during deformity procedures with minimally invasive, open, or mini-open posterior spine approaches. The implants are used to provide correction to the spine through rod reduction maneuvers.

The present system can be used in surgically correcting Adolescent Idiopathic Scoliosis (AIS), or other spinal abnormalities or injuries.

Figure 1:
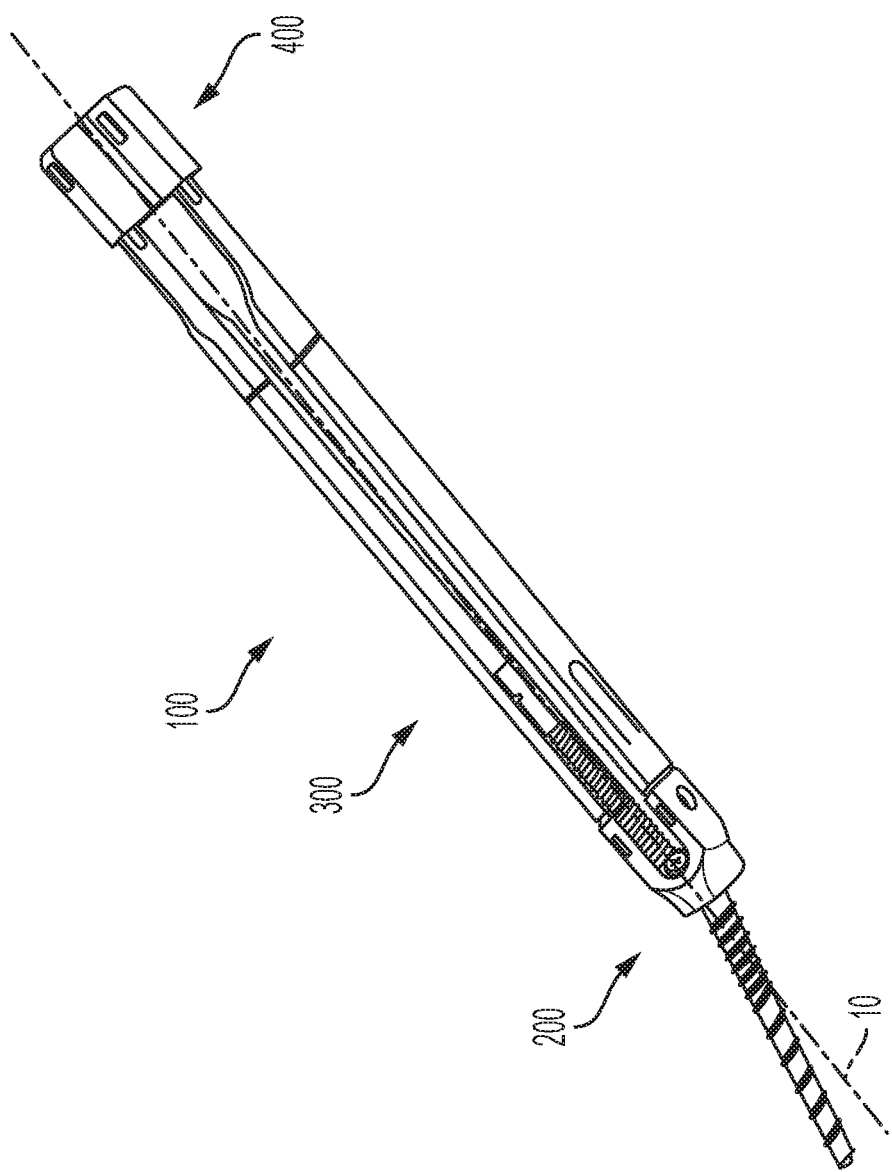
FIG. 1 is a perspective view of a capped-extender system for correcting spinal deformity, according to embodiments of the present technology.

Turning now to the drawings, and more particularly to the first figure, FIG. 1 shows a perspective view of a capped-extender system for correcting spinal deformity, according to embodiments of the present technology. The capped-extender system or assembly is indicated generally by reference numeral 100.

The capped-extender system 100 includes a bonescrew assembly 200, a pair or tab extenders 300, and a cap instrument 400. When assembled, a receiver of the bonescrew assembly, the tab extenders 300, and cap instrument 400 extend along a longitudinal axis 10 of the system 100.

Figure 2:
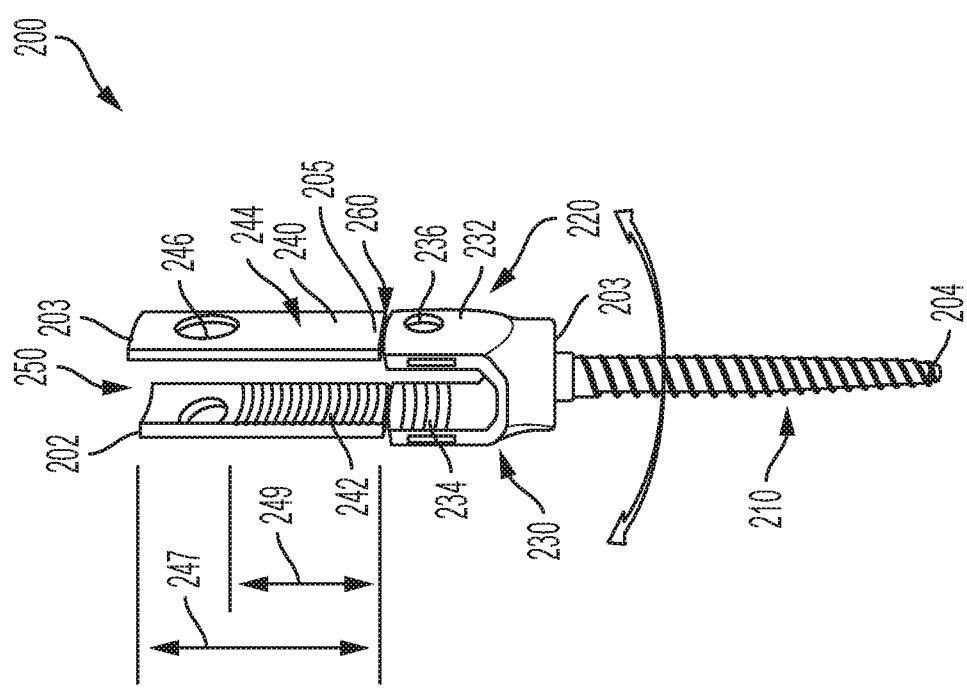
FIG. 2 is a side view of an extended-tab screw implant including a bonescrew, of the capped-extender system of FIG. 1.
Figure 3:
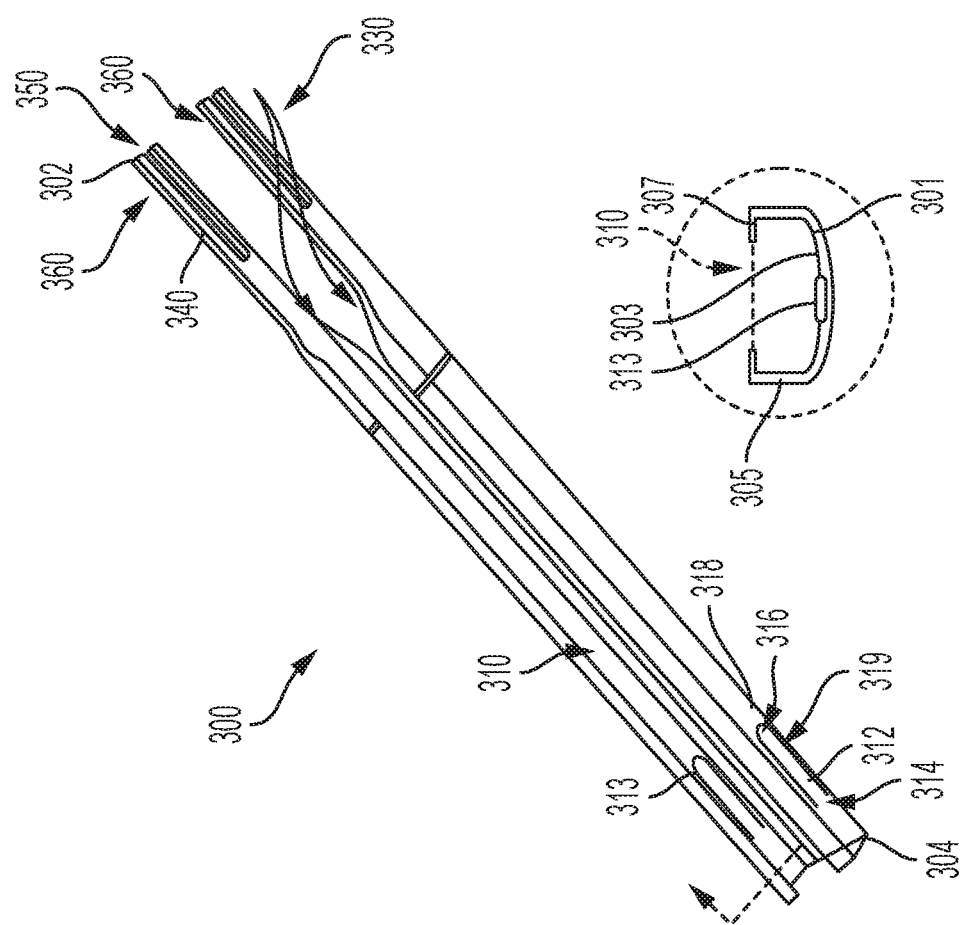
FIG. 3 is a perspective view of tab extenders of the capped-extender system of FIG. 1.
Figure 4:
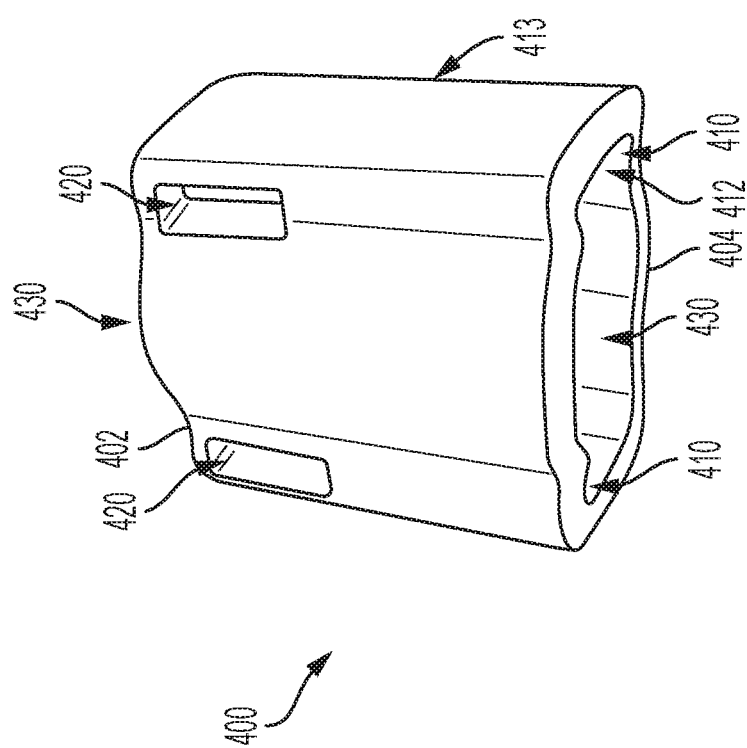
FIG. 4 is a perspective view of a cap instrument of the capped-extender system of FIG. 1.

Features of the screw assembly 200, the tab extenders 300, and the cap instrument are described further in connection with FIGS. 2, 3, and 4, respectively.

Figure 5:
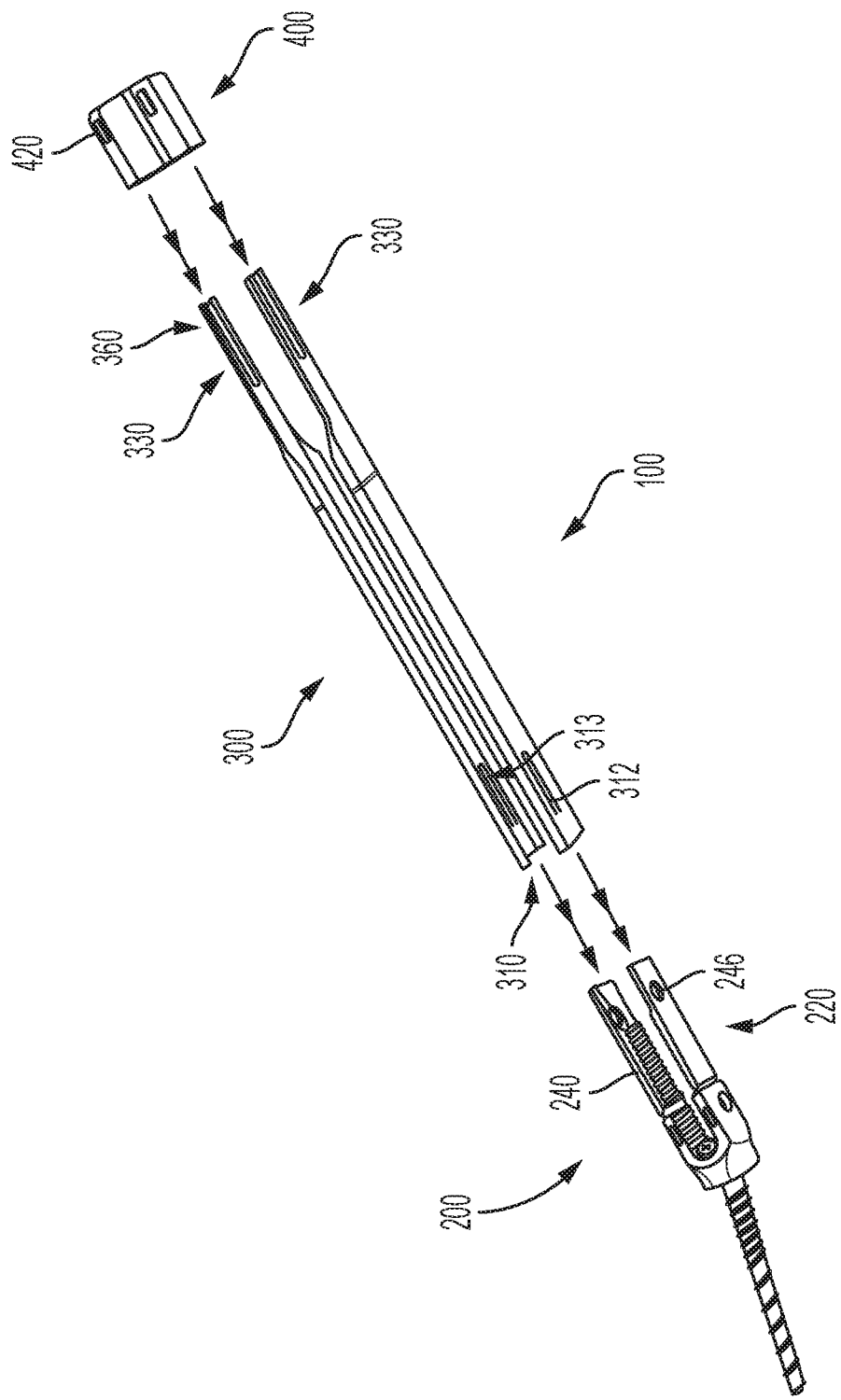
FIG. 5 is a perspective view of the capped-extender system of FIG. 1 being assembled.

Components of the system 100 can be provided (made, sold, distributed or used, for instance) in any combination, such as in one or more kits or sets. In some implementations, for instance, the screw assembly 200 is provided separate from the tab extenders 300 and cap instrument 400. And the tab extenders 300 can be provided together or separately from the cap instrument 400. In various embodiments, the system components shown in FIG. 1, or any sub-set thereof, are provided pre-assembled. FIG. 5 shows main sub-systems disassembled.

In various embodiments, any of the components can be provided in more than one size option. A user can be provided with a surgical set according to the present technology having various-sized screws 210, for instance.

FIG. 2 is a side view of the screw assembly 200. The screw assembly 200 extends from a proximal end 202 to a distal end 204.

The bonescrew assembly 200 includes a bonescrew 210 connected to a receiver arrangement 220. The bonescrew 210 have any desired or suitable format. The screw 210 has a dual-lead threadform in various embodiments. A dual-lead threadform provides robust screw-to-bone fixation.

In some cases, the bonescrew 210 and instrumentation used with the screw 210 are cannulated of fenestrated, as described more below.

The receiver arrangement 220 includes a base receiver 230 and a pair of opposing removable extender tabs 240. The receiver 230 can be referred to by other terms, such as receiver, base, or screw-assembly head.

Any of various receiver sizes can be used. The receivers 230 can be a 5.5 or a 6.0 mm receiver, for receiving a 5.5 or 6.0 mm rod, for instance.

The extender tabs 240 extend from arms 232 of the receiver 230. The opposing tabs 240 define a proximal portion of a channel 250 between them. The arms 232 of the receiver 230 define a distal portion of the channel 250.

The receiver arrangement 220 can be sized in any desired manner, for accomplishing the goals and benefits of the present disclosure. In various embodiments, the extender tabs 240 have a height 247 between a proximal end 203, corresponding to the proximal end 202 of the bonescrew assembly 200, and a distal end 205. Each tab 240 in various embodiments has a height 247 of about 16.5 mm. The extender tabs 240 each have a height anywhere within a range in some embodiments. An example range is about 16 mm to about 17 mm.

The receiver arrangement 220 can have a uni-axial, multi-axial (or, poly-axial), or fixed format. In the fixed format, the receiver 230 and the bonescrew 210 are connected so that there is no relative movement between the receiver 230 and the bonescrew 210.

For multi- and uni-axial formats, a head of the bonescrew extends into a distal cavity (not shown in detail) of the receiver, and the head is movable within the cavity.

In the multi-axial format, the receiver 230 and the screw 210 are configured and connected so that the receiver 230 can be rotated to any desired angle within a cone of space with respect to the screw 210. (Stated conversely, the screw 210 can be moved to any desired angle within a cone of possible screw movement, with respect to the receiver 230) The relative movement possible can be referred to as conical angulation.

For the uni-axial format, the receiver 230 and the screw 210 are configured and connected so that the receiver 230 can be moved only along a single plane with respect to the screw 210. (Stated conversely, the screw 210 can be moved only along the same plane with respect to the receiver 230) The plane can be referred to as a screw/receiver plane. Example movement of the screw 210 along the plane is indicated by arrow in FIG. 2. The uni-axial screw has a head secured within a distal cavity of the uni-axial receiver 230. (Screw head and cavity are not shown in detail)

The uni-axial configuration can include the screw head and the receiver 230 having corresponding flats. The screw head and receiver 230 can thus move respect to each other, with the flats touching, allowing movement of the head and receiver in the one plan, while interface at the flats keep the head and receiver from moving outside of the plane with respect to each other.

In various embodiments, one or more uni-axial screw assemblies are anchored to adjacent vertebrae, in implementation of the system 100, such that the receivers 230 can be moved only in a cephalad/caudal plane with respect to the patient.

With further reference to FIG. 2, the extender tabs 240 are connected in the receiver arrangement 220 to the receiver 230 by a breakoff section 260. The breakoff section is configured to facilitate ready, or relatively easy, breaking apart of the receiver 230 and the extender tabs 240. The breaking can be effectuated by the surgeon or robotics equipment (not shown) for instance. In various embodiments, the breakoff section 260 is configured to be readily broken, or snapped, by having material being weaker than adjacent material of the system 100, such as adjacent material of the receiver 230 and/or material of the extender tabs 240.

The breakoff section 260 can be configured in any of a variety of ways to be weaker for breaking. In some embodiments, the breakoff section 260 is weaker by being thinner than a thickness (measured from inner wall to outer wall) of one or both of (i) arms 232 of the receiver 230 and (ii) the extender tabs 240. The section 260 can instead or also be configured for ready breaking based on its material, such as by including a material that is frangible or relatively brittle (relative to the arms 232 and/or extender tabs 240).

Each receiver arm 232 has inner-surface threads 234 for receiving threads of a setscrew to secure a rod in the receiver 230. (Rods 900 are shown in FIGS. 9-12 and 14; Setscrews 1000 shown in FIGS. 10 and 14) Each arm 232 can include one or more depressions 236 promoting grasping and maneuvering of the receiver 230 by a surgical instrument (not shown). The depressions also lower weight instrument weight, without compromising strength of the arms 232, and lower the amount of material required for making the receivers 300.

An outer surface 244 of each extender tab 240 forms a locking aperture 246. In various embodiments, the aperture 246 extends fully through the wall of the tab 240, between the outer surface 240 and an inner surface of the tab 240.

The locking aperture 246 is sized, shaped, and positioned to receive a protrusion 316 of a mating locking component 312 of the tab extender 300. The locking aperture 246 is positioned proximal of a proximal end of the extender-tab threadform 242 in some embodiments, as shown in FIG. 2.

As each tab extender 400 is moved distally and partially around or against the proximal end portion 203 of the corresponding extender tab 240, the extender tab 240 slides into a channel 310 of the tab extender 300. In this step, a node or protrusion 313 of the locking component 312 slides along the outer wall 244 of the extender tab 240 until the protrusion 313 reaches the locking aperture 246 of the extender tab 240. As the extender tab 240 is moved further into the tab extender 300, the protrusion 313, being biased inward by action of the spring-type extender locking component 312, is pushed into engagement with the locking aperture 246, releasably locking the tab extender 300 to (onto) the extender tab 240.

The extender locking component 312 and extender tab 240, including aperture 246, are configured such that a user—a surgeon or sensor device, for instance—receives one or both of tactile and audible feedback, such as an audible and haptic click, when the engagement protrusion 313 of the tab extender 300 pops into the locking aperture 246 of the extender tab 240.

Figure 10:
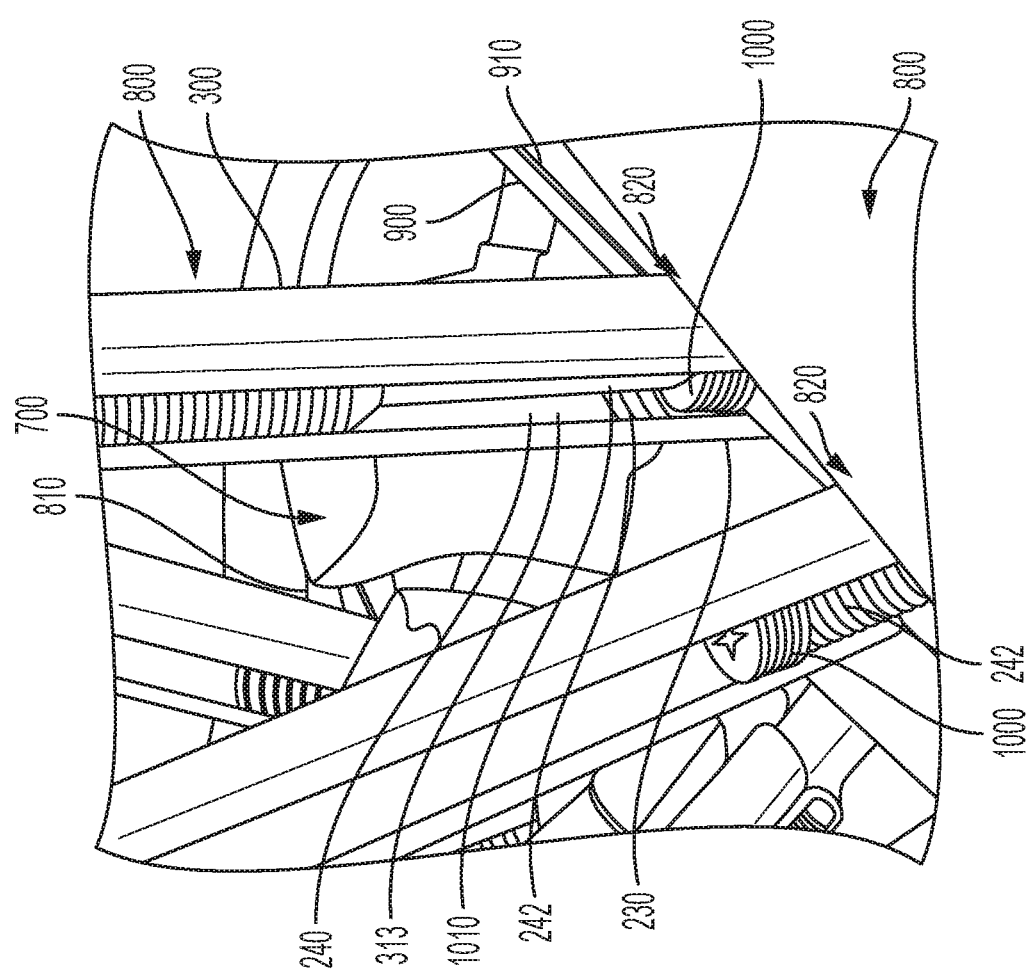
FIG. 10 is a close-up perspective view showing provisional tightening of setscrews into the extender tabs of the capped-extender system.
Figure 14:
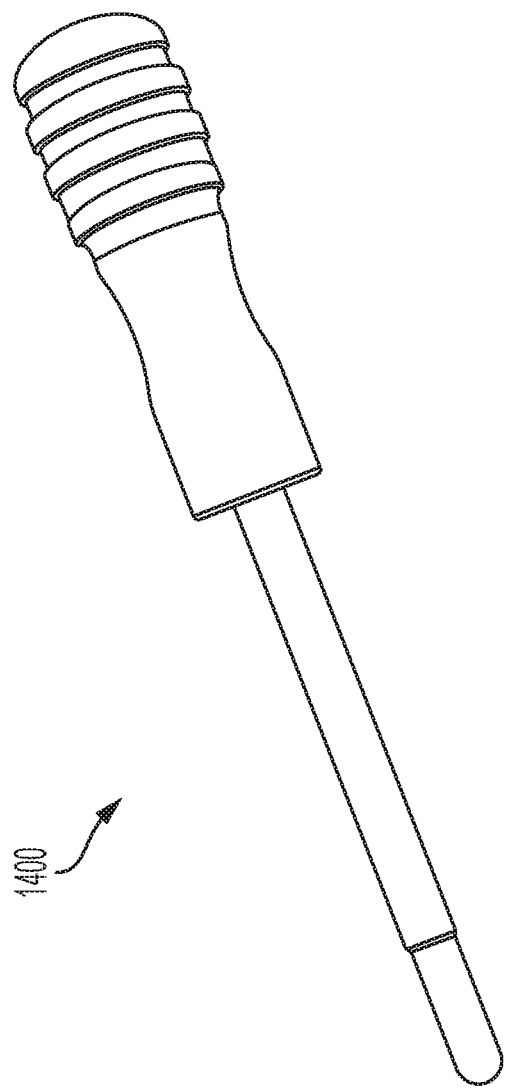
FIG. 14 shows a perspective view of an example dual-tab-breaking instrument.

The extender tabs 240 have inner-surface threads 242 sized and shaped for receiving a setscrew (reference 1000 in FIGS. 10 and 14). The tab threads 242 are clocked to the receiver threads 234, and sized and shaped like the receiver threads 234, so that the setscrew can be threaded readily or smoothly from the tab threads 242 distally onto the receiver threads 234.

The tab threads 242 in various embodiments begin at or adjacent a distal end 205 of the extender tab 240, where the breakoff section 260 starts. The tab threads 242 in various embodiments extend proximally from the distal end 205 by any desired or suitable distance, which can be referred to as a tab-thread height 249. In various embodiments, the tab-thread height 249 is at least half of the height 247 of the extender tab. In some embodiments, the tab-thread height 249 extends from the distal end proximally along at least about two-thirds of the height 247 of the extender tab. The tab-thread height 249 is in various embodiments between about 8 mm and about 14 mm.

In various embodiments, the extender-tab threads 242 extend from the distal end 205 proximally to at or adjacent the locking apertures 246. In these embodiments, the higher the apertures 246 are on the tabs 240, the greater the thread height 249. In a contemplated embodiment, the tab threads 242 extend higher than a lower, or distal edge of the apertures 246. In these embodiments, portions of the thread are present on both sides of the apertures 246. The thread 242 can also extend to a top, or proximal edge of the apertures 246, and beyond, including up to terminating proximally at or adjacent the proximal end of the tabs 203.

FIG. 3 is a perspective view of a pair of tab extenders 300 of the capped-extender system 100. The extenders 300 are selectively attachable to and removable from the extender tabs 240 of the screw assemblies 200.

The tab extenders 300 are in various embodiments reusable. While the bonescrew 210 and receiver 230 are implants, left in the patient, the extender tabs 240 and tab extenders 300 are removed. The tabs 240 and extenders 300 are removed together, by maneuvering the tabs 240 and/or extenders 300, which are connected to the tabs 340, to break material of the breakoff section 260.

The tab extenders 300 each extend from a proximal end 302 to a distal end 304. Each extender 300 includes a channel 310 extending from a distal opening at or adjacent the distal end 304 of the extender 300 to a proximal opening 320. The channel 310 is sized and shaped to engages or receive at least a portion of the extender tab 240 snuggly.

The channel 310 is formed by inner walls 301 of the tab extender 300. The inner walls are shaped to form the channel 310 having has a generally u-shaped profile, in various embodiments, as shown by the main view and cross-sectional inset in FIG. 3.

In some cases, the walls 301 forming the u-shaped channel include a back wall 303, side or lateral walls 305, and shoulders or protruding walls 307 extending inward from the lateral walls 315. The lateral walls 305 and the protruding walls 307 help ensure that the extender tabs 240 are, once received in the channel 310, maintained in the channel 310 until the user removes them.

Channel geometry can also ensure that the outer walls 244 of the extender tabs 244 are generally flush, or slide along, the corresponding back walls 303 of the tab extenders 300. In this way, the extender protrusion 313, being biased inwardly (toward a system central axis), will surely engage with the locking apertures 246 of the extender tabs 240 when the tab extenders 300 are slid distally far enough on or along the extender tabs 240.

In a contemplated embodiment, the shoulders 307 extend fully toward each other, forming a single wall, opposite the back wall 303, as indicated generally by dashed line in the inset of FIG. 3.

The back wall 303 is in various embodiments curved, as shown by the inset of FIG. 3. The curve corresponds to a curve in the outer surface 244 of the extender tab 240. The corresponding curves promote flush engagement, or sufficient inter-surface sliding, between the back wall 303 of the extender 300 and the outer surface 244 of the tabs 240. Engagement of the protrusion 313 into to locking aperture 246, when the tab extenders 300 are slid distally far enough on or along the extender tabs 240, is also thereby promoted.

The tab-extender locking component 312 in various embodiments extends from a distal end 314 to a proximal end 316. The extender locking component 312 is in various embodiments connected to a balance of the extender 300 only at the distal end 314. The extender locking component 312 is at other portions separated by a space 319 from adjacent portions 318 of the extender 300.

The extender locking component 312 is in various embodiments configured as a spring, biasing the protrusion 313 inward, toward the extender tab 240 that becomes positioned in the channel 310 of the tab extender 300 for use of the system 100. The extender locking component 312 can be a type of linear flex spring, such as of the cantilever type.

In various embodiments, each tab extender 300 includes a cap-engaging end portion 330. The cap-engaging end portion 330 can be configured (e.g., size, shape, material) in any of a variety of ways suitable for engaging with the cap instrument 400. The cap-engaging end portion 330 can have a forked configuration, as shown in FIG. 3, for example. The forked configuration has a pair of opposing prongs 340 separated by a space 350. The fork prongs 340 can each include an engagement protrusion or node 360 for engaging with engagement openings 420 of the cap instrument 400 (FIG. 4). The fork prongs 340 can be referred to by other terms, such as tines, fork arms, fork tips, or the like.

Turning now to FIG. 4, a perspective view shows an example cap instrument 400 of the capped-extender system 100. The cap instrument 400, or cap, extends from a proximal end 402 to a distal end 404.

The cap 400 has two extender-receiving channels 410, each sized, shaped, and positioned to receive all or some of the cap-engaging end portion 330 of a tab extender 300. The cap 400 has an inner surface 412 defining a portion each extender-receiving channel 410. The inner surface 412 also defines in each extender-receiving channel a set of opposing engagement openings 420. It should be appreciated that FIG. 4 shows one of each set of opposing engagement openings 420, expressly, and that a mating opening 420 for each pair is on an opposite side of the cap (opposite the perspective in FIG. 4). The engagement openings can extend fully through the cap 400, from the inner wall 412 to an outer wall 413, as shown in FIG. 4.

The inner walls 412 of the cap instrument 400 also define an axis-instrument, or guide, channel 430. The instrument channel 430 is in various embodiments central to the cap, and generally centered on the longitudinal axis 10 of the system 100. The guide channel 430 is sized, shaped, and positioned for receiving one or more instruments in operation of the system 100, as described further below. The guide channel 430 can be sized and shaped to help guide the instruments, such as directly along the system axis 10 and to the bonescrew 210 or setscrew 1000 (FIGS. 10 and 14). The cap instrument 400 can thus be referred to as a guided cap, cap guide, or the like.

The setscrews 1000 are in various embodiments non-breakoff setscrews. These are lower-profile (are shorter) than breakoff setscrews.

Reference is now made to FIGS. 3 and 4 to describe engagement between the tab extender 300 and the cap instrument 400 further.

Each fork arm 340 can act as a spring, biasing its engagement node 360 outward, away from the inter-prong space 350. Each fork arm 340 can be a type of linear flex spring, such as of the cantilever type.

When the cap instrument 400 is being engaged with the forked engagement end portion 330 of the tab extender 300, the protrusions 360, and so the forks 340 of the extender 300 are pushed slightly in, toward the inter-prong space 350, making the space 350 smaller).

As the cap instrument 400 is moved distally onto the proximal end portion 330 of the tab extender 300, with the forked arms 340 sliding into channel 410 of cap 400, each set of opposing fork nodes 360 slides along the inner wall 412 of the cap 400 until the nodes 460 reach the engagement openings 420 of the cap 400. As the forked arms 340 are moved further into the cap 400, the opposing nodes 360, being biased outward by the spring-action of the forked arms 340, are pushed into engagement with the cap engagement openings 420, releasably locking the cap 400 to the tab extenders 300.

As referenced, the cap-engaging end portion 330, including in various embodiments the formed arms 340 and their engagement nodes 360, and the cap instrument 400, including the engagement openings 420, are configured such that a user—e.g., surgeon or sensor device—receives tactile and audible feedback, such as an audible and haptic click when the engagement nodes 360 click in the engagement openings 420.

The cap instrument 400, along with functioning to guide instruments though its central guide channel 430, counteracts a tendency that the extenders 300 may have to splay, at least at the proximal ends 330, to splay. The cap 400 holds the opposing tab extenders 300 from moving away from each other.

FIG. 5 is a perspective view of the capped-extender system 100 being assembled. As shown, opposing tab extenders 300 are engaged to the extender tabs 240 of the screw assembly 200. The cap instrument 400 is engaged to the engagement end 330 of the tab extenders 300. In various embodiments, the cap 400 is attached to the extenders 300 after the extenders have been connected to the screw assembly 200.

Figure 6:
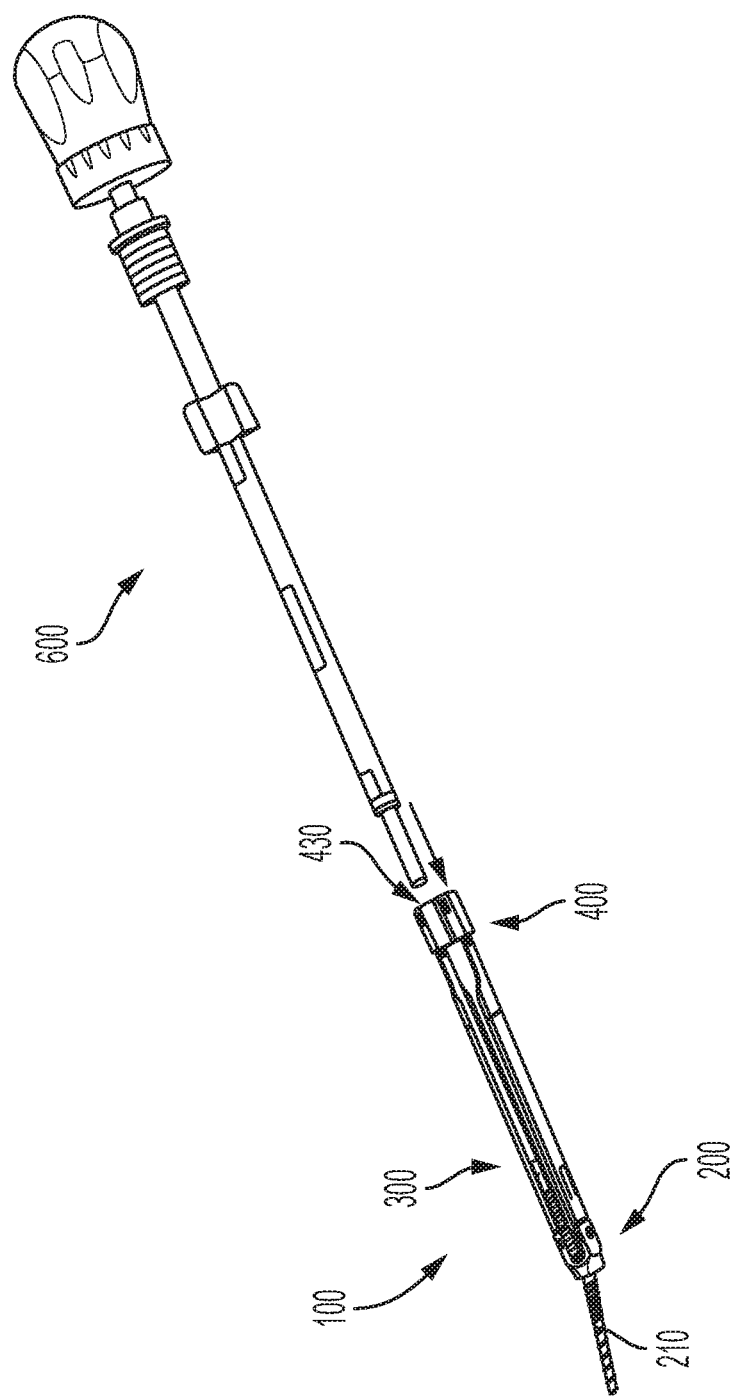
FIG. 6 is a perspective view of a bonescrew driver being positioned to drive the screw of the assembled capped-extender system of FIG. 1.
Figure 7:
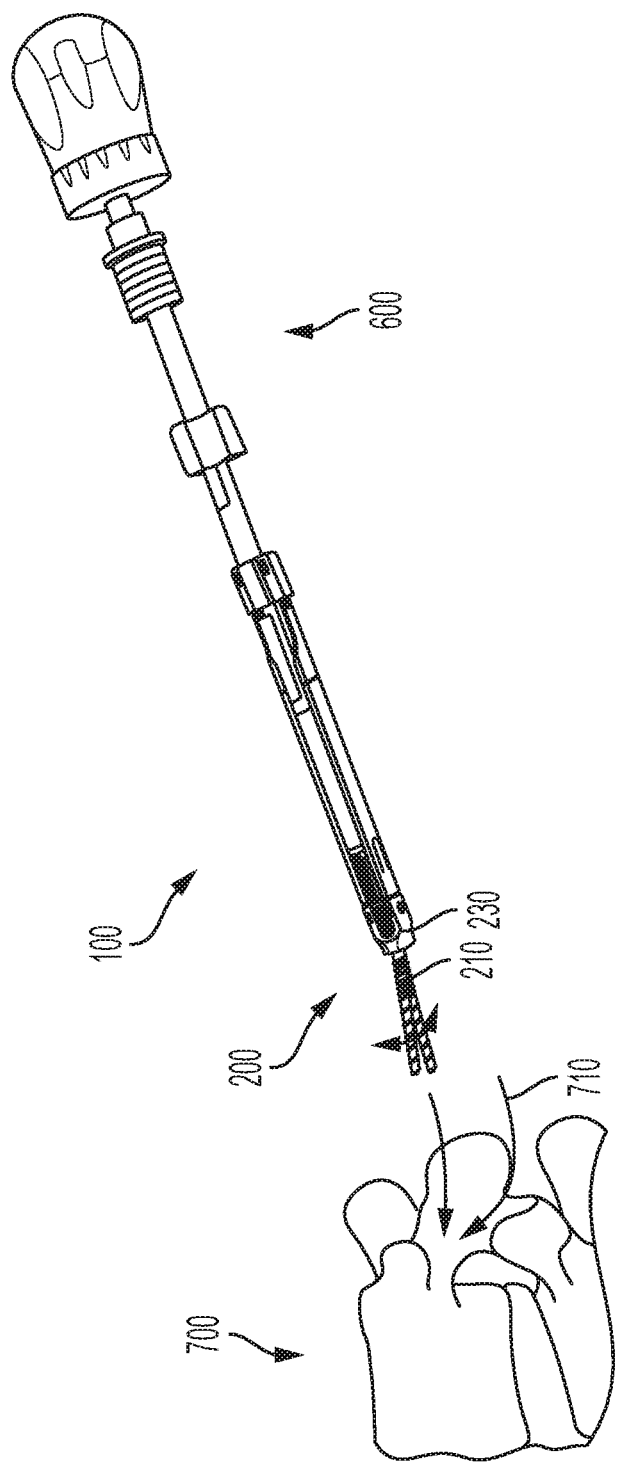
FIG. 7 is a perspective view of the bonescrew driver fully inserted into the assembled capped-extender system, and positioning the arrangement for driving the bonescrew into a pedical pedicle of a patient vertebra.

In use of the system 100, the bonescrew 210 is anchored to a patient vertebra 700 (FIG. 7). A user anchors the bonescrew using a bonescrew driver. An example driver 600 is shown in FIG. 6. A distal end of the driver is sized and shaped to engage a bonescrew head, which is not visible in FIGS. 6 and 7. For embodiments in which the bonescrew 210 is cannulated, a cannulated bonescrew driver can be used, such as a cannulated retaining bonescrew driver.

The driver 600 is inserted through the guide channel 430 of the cap 400, and between the opposing tab extenders 300 held together by the cap 400. The driver 600 is moved farther distally until its tip seats in the head of the screw 210.

FIG. 7 is a perspective view of the bonescrew driver 600 fully inserted into the assembled capped-extender system 100. The screw assembly 200 can have a multi-axial, fixed, or uni-axial configuration, as referenced. Example axial motion of the screw 210 with respect to the receiver 230 is indicated in FIG. 7 by the curved double-arrowed line. The line is considered to represent, in the alternative, uni-axial motion and multi-axial movement (depending on whether the assembly 200 has the uni- or multi-axial format).

The system 100 is maneuvered in preparation to drive the bonescrew 210 into a portion of the patient vertebra 700. Movement of the screw 210 toward insertion point of a vertebra 700 is shown in FIG. 7 schematically by single-arrowed line. In various embodiments, the screw 210 is guided to and driven into a pedical pedicle portion 710 of the vertebra 700.

Prior to screw driving, a bone tap (not shown) can be used to prepare a hole into which the screw 210 will be driven. For embodiments in which a cannulated screw 210 is used, a cannulated tap can be used.

A plurality of capped-extender systems 100 are driven into adjacent vertebra 700. Driving the bonescrew 210 can be accomplished by a surgeon or robotics equipment (not shown). The driving can be performed using a powered surgical instrument, such as a powered driver, for instance.

Figure 8:
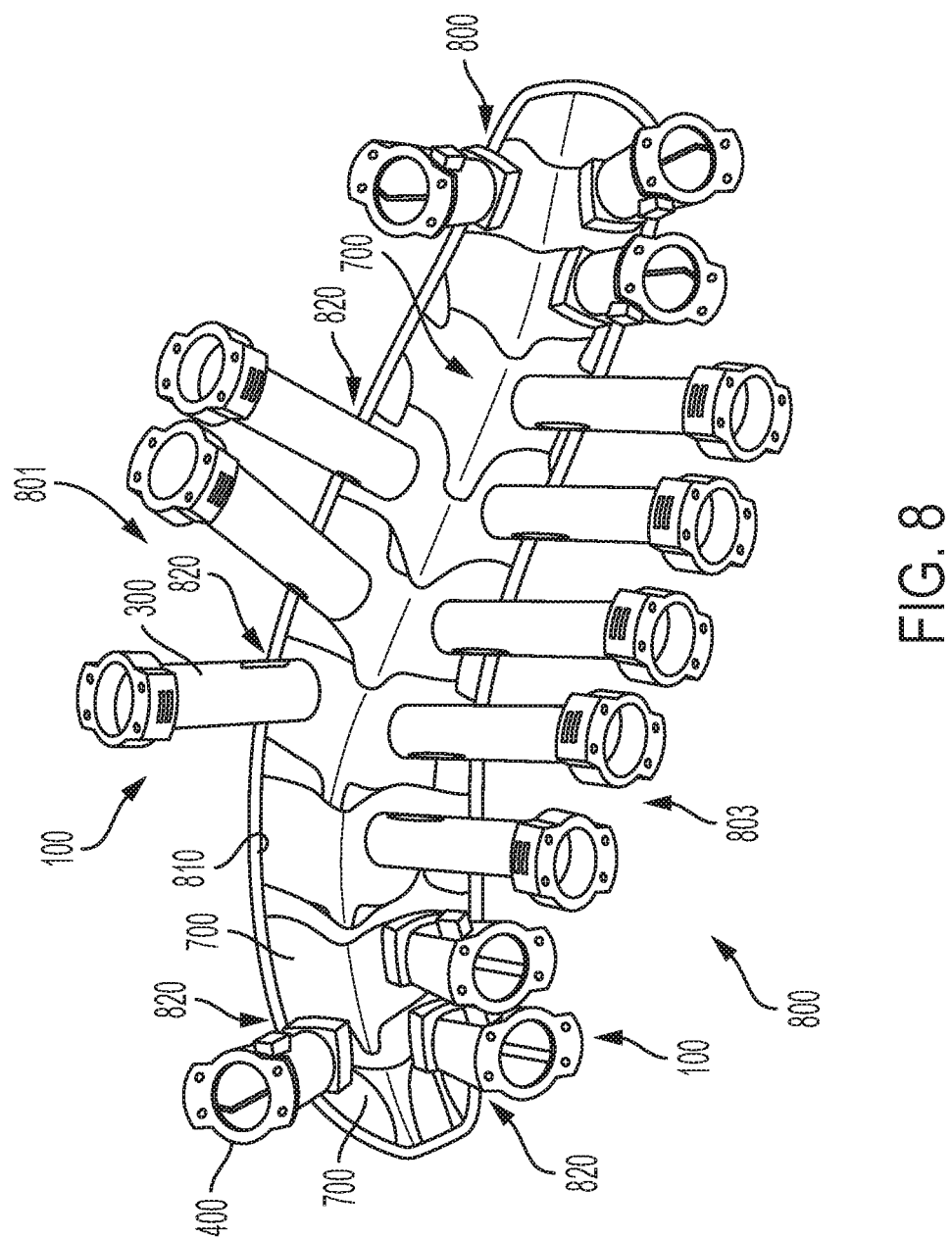
FIG. 8 is a top, plan, view of lumbar vertebrae of a patient spine and a plurality of capped-extender systems anchored thereto.

FIG. 8 is a top, plan, view of lumbar vertebrae 700 having the plurality of capped-extender systems 100 anchored thereto.

In various embodiments, the systems 100 are implanted in a specific order. When a subject section of spine is undesirably curved away from a line, the two sides of the vertebrae 700 departing from the line can be instructive. Such curve is shown in FIG. 8. The sides of the vertebrae 700 can be referenced with respect to the curve, namely as a convex side 801 (the side facing up in the view of FIG. 8) and a concave side 803 (facing downward in the view). The concave side 803 can also be referred to as the primary reduction side, and the convex side 801 as the secondary reduction side.

In various embodiments, systems 100 are placed first on the primary, concave side 803 of subject vertebra. While in some embodiments, it a user may determine best to start on the convex side 801, starting on the concave side 803 is described primarily herein.

In a contemplated embodiment, systems 100 are inserted on both, concave and convex sides, such as by first implanting a system 100 into each side 801/803 of a caudal-most vertebra 700. Systems 100 can be implanted in an alternating manner, such as by first implanting one on one side of a caudal-most subject vertebra 700, followed by implantation of one on the other side of a cranial-most subject vertebra 700, followed by implanting systems 100 on the other sides of the caudal-most and cranial-most subject vertebra or into an apical vertebra. The apical, or apex, vertebra is the vertebra 700 at which the undesired curve of the spine is at its maximum.

It is in some embodiments preferred that the systems 100 be implanted starting with a caudal-most subject vertebra 700 on the concave side 803. The second and third systems 100 implanted are in various embodiments implanted to a cranial-most subject vertebra 700 and an apex vertebra 700 on the concave side 803.

Implanting initial systems 100 to such strategic positions has benefits including promoting increased visibility and locating for subsequent system 100 implantations. Spacing systems 100 from each other in the initial system implantations also helps ensure that the towers of the initially implanted systems do not interfere with each other.

Any of the systems 100 implanted, and especially systems 100 implanted initially in strategic locations, such as those mentioned (caudal-most, apical, and cranial-most), can also retract tissue, such as skin and other soft tissue of the patient 800. The retraction function of the systems 100 promotes visibility and maneuverability in the patient 800 during the procedure. An incision edge is referenced in FIG. 8 by numeral 810. Tower-retraction points are referenced by numeral 820 at system-incision interfaces. The functionality is especially useful in minimally invasive, or mini-open, surgeries, for which space and visibility are especially limited by design. The retraction function of the reduces the need for separate retractor instruments (not shown), and in some cases can obviate need for separate retractors all together, saving equipment cost (product, distribution, storage, for instance), and work and time in the procedure.

In various embodiments, after a caudal-most system 100 is implanted first on the concave side 803, the next system 100 implanted is implanted into the concave side 803 of a second caudal-most subject vertebrae 700. Implantation of subsequent systems 100 can continue sequentially moving cranially. Or, after the first caudal-most implant is place, the next two implants can be placed on the concave side 803 at a cranial-most vertebra and an apical vertebra, in either order.

In some other embodiments, after a cranial-most system 100 is implanted first on the concave side 803, the next system 100 implanted is implanted into the concave side 803 of a second cranial-most subject vertebrae 700. Implantation of subsequent systems 100 can continue sequentially moving caudally. Or, after the first cranial-most implant is place, the next two implants can be placed on the concave side 803 at a caudal-most vertebra and an apical vertebra, in either order.

In various embodiments, after a caudal-most system 100 is implanted first on the concave side 803, the next system 100 implanted is implanted into the concave side 803, of a caudal-most, cranial-most, or apical vertebra 700.

In various implementations, after inserting all of the systems 100 needed for the procedure, heights of the various towers (e.g., levels of the caps 400) should be at approximately the same height outside the patient 800.

Once all systems 100 are implanted, the user can confirm placement and positioning radiologically, such as by taking an x-ray to confirm screw placement and positioning. A blue towel placed between the towers may be helpful to hold them apart for this. Placement and position can also be confirmed using a nerve-monitoring system.

Once correct system 100 placements have been verified, a user can measure and contour selected rods considering the present and target spinal orientations. Present and target orientations can be represented with respect to the patient's sagittal and coronal planes.

Figure 9:
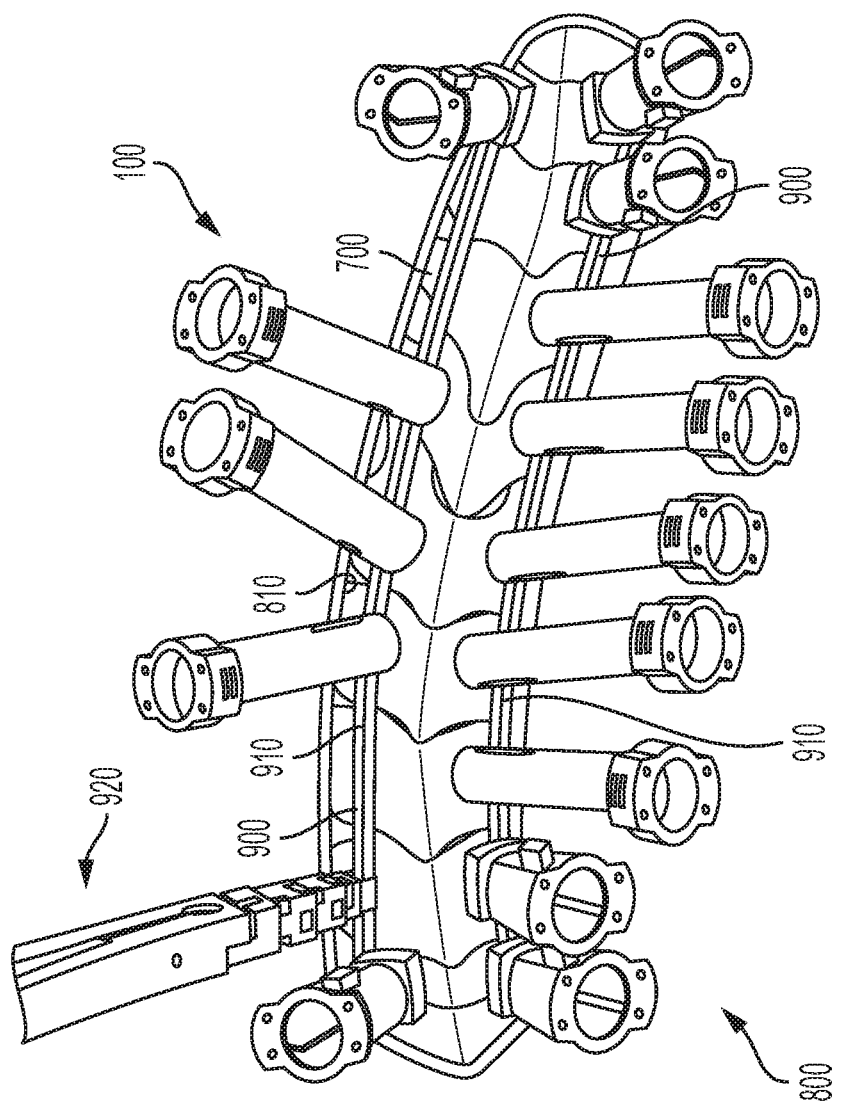
FIG. 9 is the view of FIG. 8 with pre-bent rods positioned provisionally through the extender tabs of the capped-extender systems anchored to the vertebrae, prior to introduction of a setscrew into each capped-extender system, and provisional tightening of the setscrews into the extended tabs toward the rods.

FIG. 9 is the view of FIG. 8 with spinal rods 900 positioned provisionally through the implanted systems 100. The rods 900 can be pre-bent, before insertion, using rod benders (not shown), for example. In various embodiments, each rod has a visible orientation reference line 901 formed thereon or therein. The line 901 can be formed by etching, inking, or other manner of marking. The user can in referencing the line 901 in the bending, considering how she would like the rod, and so the line, orientated when the rod is secured subsequently in the systems 100.

The user can clamp the rods 900, such as at or adjacent rod ends to a static construct. to facilitate rod contouring. Clamping can help prevent unwanted rod rotation or other movement during contouring. Another method of securing the rod for bending is to connect a hex wrench to the rod end as a reference, and then use rod benders, such as in-situ benders, to contour the rod 900. The rods 900 can be contoured before and/or after they are placed in the systems 100.

The rods 900 can be inserted using any suitable instrument, such as a type of rod gripper 920 or percutaneous (perc) inserter instrument.

The rods 900 are in various embodiments inserted starting at a first system 100, such as a caudal-most system 100. When lined rods are used, the lining can be used in orientating the rods for and during initial insertion. The lines 901 can be used to position the rods in a provisional position, to be re-oriented later to a final positioning, such as by the rod gripper 920, and locked in place by setscrews 1000 (FIGS. 10 and 14).

FIG. 10 is a close-up perspective view showing provisional tightening of setscrews 1000 into the extender tabs 240 of the capped-extender system 100.

As with benefits of implanting the systems 100 in particular order, benefits can be accomplished by inserting the setscrews 1000 in a select order. In various embodiments, a user places the setscrews 1000 starting at the caudal and cranial ends of the rods 900. In some embodiments, the first, or one of the first, setscrews provisionally inserted can be an apical screw—i.e., into the system 100 at the apex of the curve being corrected by the procedure.

A provisional driver 1010, such as a swizzle stick, can be used to insert the setscrews 1000 provisionally (not fully tightened) into the extender tabs 240, or even initially into the receiver 230.

Figure 11:
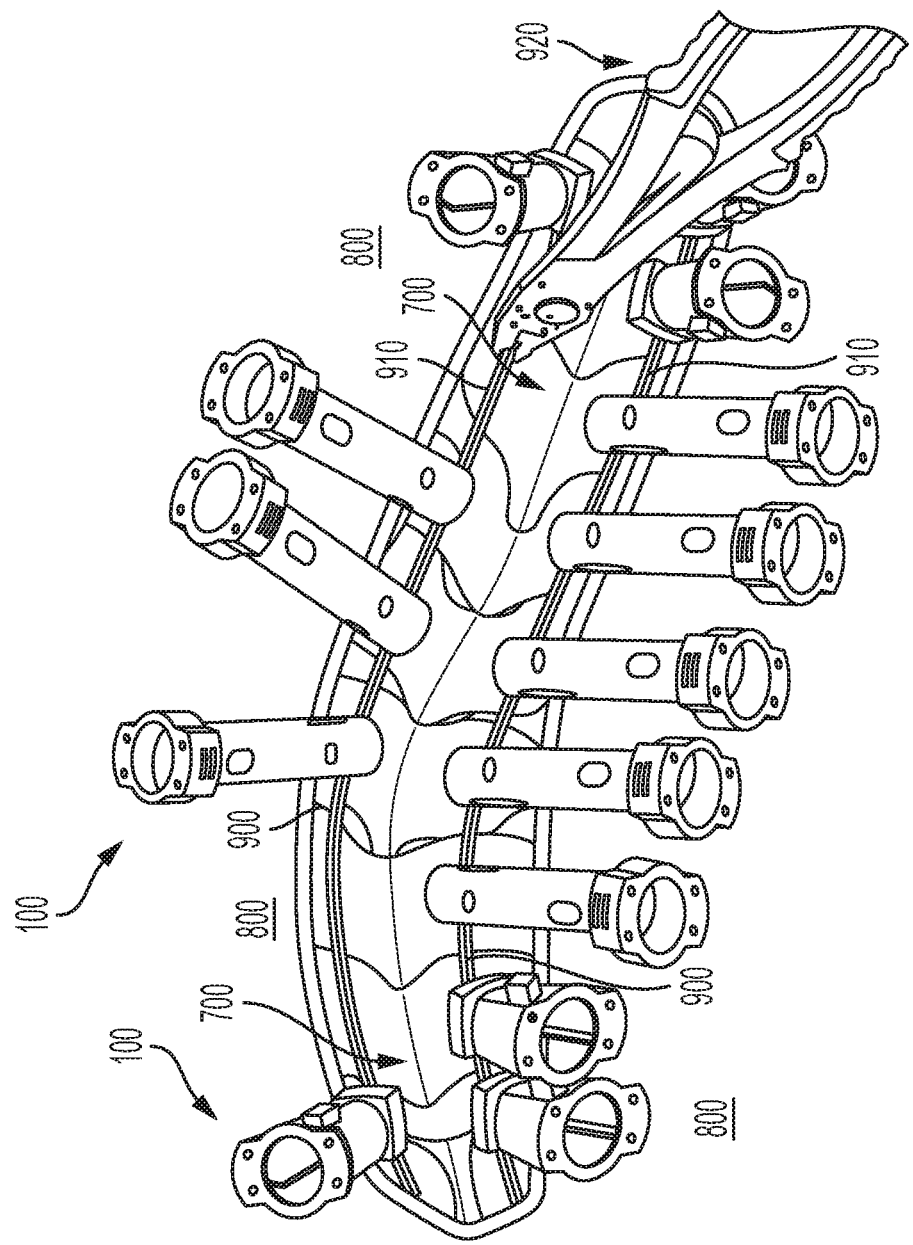
FIG. 11 is the plan view of FIG. 9 showing rotating of the rod using a rod gripper, to adjust the spine into the desired orientation, such as a normal, kyphosis, orientation.

FIG. 11 is the plan view, like that of FIG. 9, showing the rods 900 being rotated using a rod gripper 920, to adjust the spine into a desired orientation. This may include adjusting or positioning the rods to promote a normal kyphosis, or a more normal kyphotic curve for the spine. The concave- or primary-reduction rod (lower in the view of FIG. 11) can be oriented first, or the secondary, convex rod can be oriented first. The user can as mentioned use the orientation lines 901 in orientating the rods 900, to ensure desired orientation of the rod contour in the systems 100 and patient 800.

Once proper orientation is achieved, the user can hold the rods 900 in place with the rod gripper 920 during setscrew 900 starting or continuation, and thereby rod reduction or further rod reduction—reducing the rod 900 toward its eventual final position seated in the receiver 230.

Once the rod 900 is secured, the user can further rotate the rod 900 in the sagittal plane, using the rod gripper 920 and the line 901 for reference, toward or to final position, which can include normal kyphosis. The user then secures the rod 900 by further threading the setscrew 1000 down, into the threads 234 of the receiver 230. This securement can be performed first at a caudal end of the construct.

In some embodiments, a user secures the rods 900 in a manner specific to a type of patient condition. For a patient 800 having a double-thoracic-curved spine, for instance, the user may secure the rod 900 at the cranial end first (upper thoracic curve area), before moving to locking down the rod 900 at or toward the caudal end (lower thoracic curve area).

In some implementations, the user translates the construct (formed, e.g., by all of the extenders and rods) by compression and/or distraction. For translation, a surgeon or assistant can apply reduction force on the apical system/s 100 to induce some rotational force on the construct, there, and so on the local spine. The user can consider for any further reduction or adjustments (e.g., rod bending) there or at other systems 100, a remaining reduction distance between the apex and the rod 900.

The user can then secure down remaining setscrews 1000 into the other systems 100. The user can work in towards the middle of the apex when inserting remaining setscrews 100. It can be helpful to reduce (thread the setscrew further down on the rod 900 in the systems 100) at the caudal ends of the rod 900 before reducing apical setscrews 1000. The user can then move up and down the concave side, using a turn or half turn of the setscrew 900 to pull the spine to or toward the rod shape.

Once all setscrews 900 are secured in place, the user can move up and down the concave side turning each setscrew 1000 a turn of half a turn depending on the tension of translating the spine up to the rod 900. This movement, up and down the spine, balances power of reduction across the multiple anchor sites. The user moves up and down the concave-side 303 rod 900 until all of the setscrews 1000 are reduced.

The user can add rotational force on the concave systems 100 to maximize reduction.

Once primary reduction is complete on the concave rod 900, the user can ensure that the convex screws 900 are at least provisionally, and in some cases firmly, tightened to the rod. Once the rod 900 has been reduced and/correction has been achieved, the user can use x-ray and/or nerve-monitoring to confirm screw placement/position.

In some implementations, the user may perform an optional rod reduction process, such as by using a rod-reducing instrument (not shown). The user reduces the rods 900 using the rod reducers sequentially along each. The reducer may include a window for use in maneuvering/orienting the rods 900. The user can, for instance, ensure that the marked line 901 when viewed through the window lines up with a first, initial indication/s at or adjacent the window. Location of the line 901 in the rod-reducer window during reduction indicates how close the rod 900 is to being fully reduced.

The rod 900 can be manipulated as needed by loosening one or more setscrews 1000, such as at the cranial end of the construct. The rod reducer can be sized and shaped corresponding to size and shape of a portion of the extenders 300. The reducer can be configured to be able to be slide over a pair of extenders 300, for instance. For inserting the rod reducer, the user in some embodiments removes the corresponding cap 400 and slides the reducer over the un-capped extenders 300.

The user may with the rod-reducing instrument use an additional instrument to facilitate rod reduction. The user can use a nut driver, for instance, such as one having a quick-connect ratcheting-egg handle, such as by attaching it to a top of the rod reducer to more easily reduce the rod 900.

The rod 900 is reduced using the rod reducer until the rod line 901 corresponds to a second, reduced, indication of the rod reducer, indicating that the rod 900 has been fully reduced into the receiver 230.

If using rod reducers, a long setscrew driver may be used in conjunction with the rod reducers for final setscrew tightening.

Figure 12:
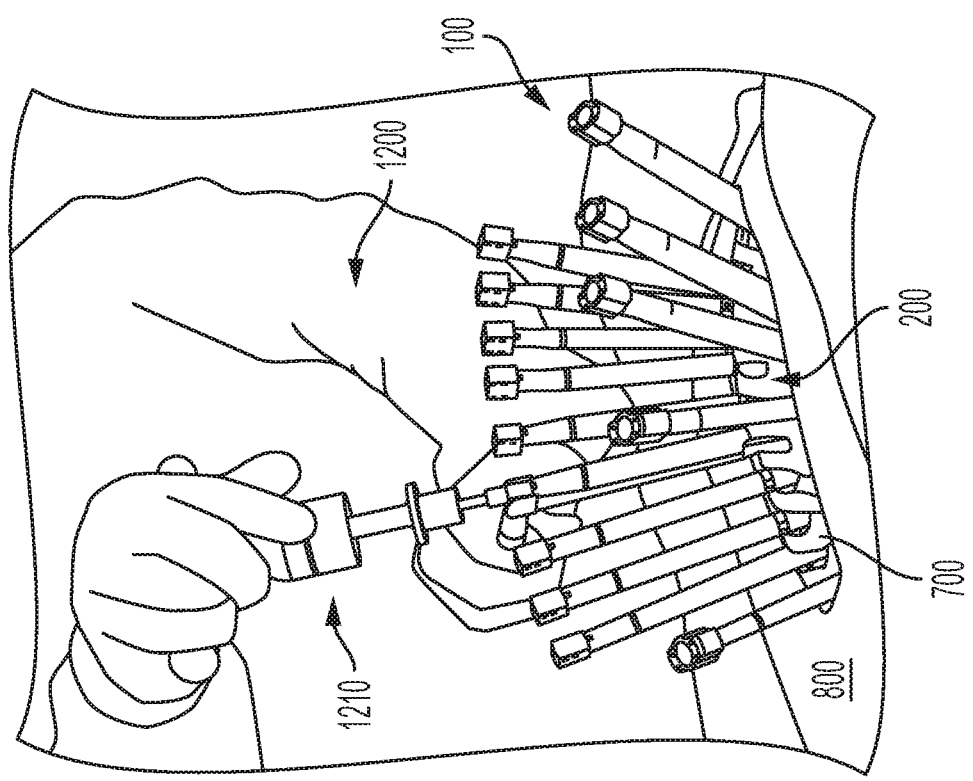
FIG. 12 is a perspective view of a surgeon finally tightening the setscrews.

FIG. 12 is a perspective view of a surgeon 1200 finally tightening the setscrews 1000 (visible in FIG. 10, not visible in FIG. 12). Final tightening is performed after bonescrew-assembly placement has been confirmed. This technique helps users ensure that the bonescrew assembly 200 and the rod 900 are normalized to one another and allows for the rod 900 to be fully seated in the receiver 230 in the final tightening.

The final tightening can include finally tightening the setscrews 1000 using a ring counter-torque instrument 1210.

Figure 13:
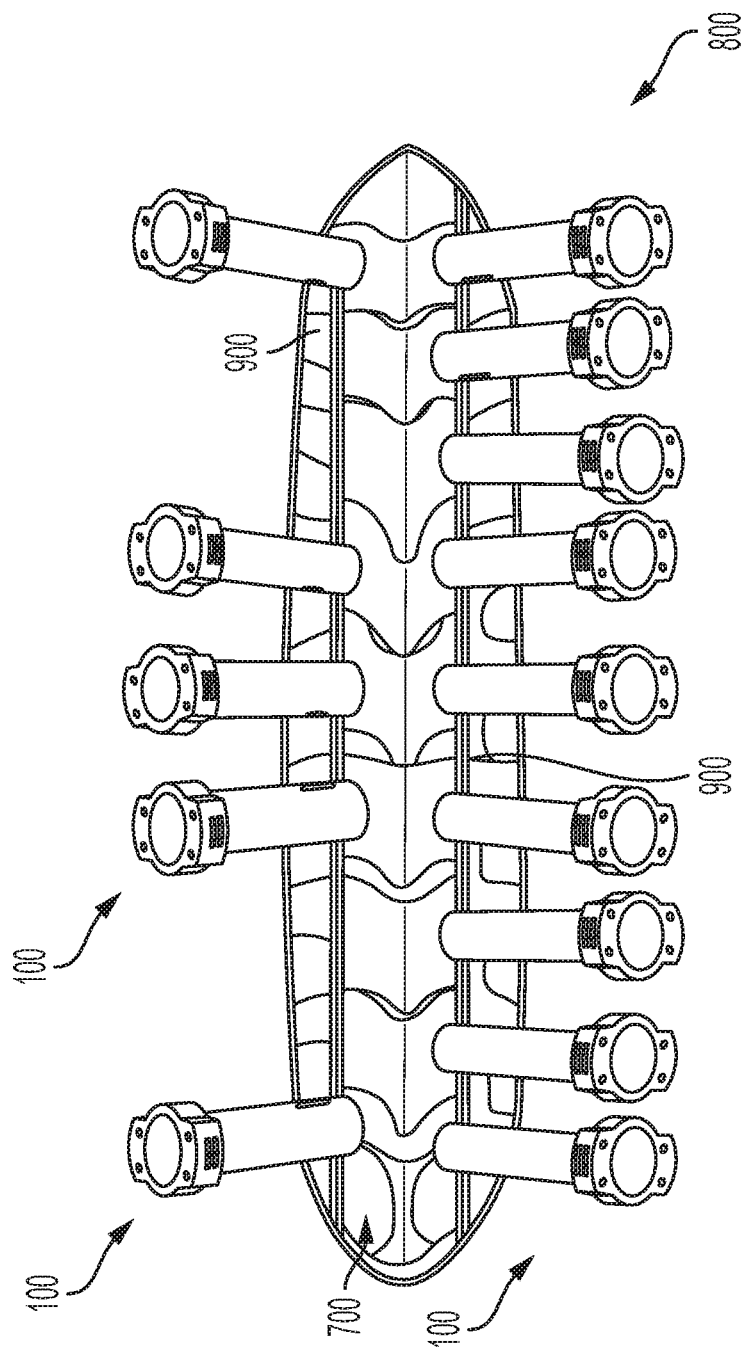
FIG. 13 is the plan view showing the vertebrae having been oriented to be generally straight in the longitudinal, or sagittal, plane.

FIG. 13 is the plan view showing the vertebrae 700 having been oriented to a desired orientation, generally straight in the longitudinal, or sagittal, plane.

After final tightening of the setscrews 1000, the user breaks each implant at the break-off sections 260 connecting the receiver 230 to the extender tabs 240 (FIG. 2). In so doing, for each system 100, the two extender tabs 240, the pair of tab extenders 300, and the cap 400, if the cap is still attached to the extenders 300, are removed together.

To effectuate the breaking off, the user can use a tab-breaking instrument. FIG. 14 shows a perspective view of an example dual-tab-breaking instrument 1400. The user inserts the dual-tab-breaker 1400 through the cap 400, if still present, until fully or sufficiently seated or positioned in the system 100, and then forces the instrument 1400 so that the extender tabs 240 break from the receiver 230 at the breakoff sections 260. Moving the instrument 1400 can include pushing medially, pulling laterally, and then pushing medially for breakoff, for instance.

Once broken off, the extender tabs 240 and tab extenders 300 can be disassembled, as well as the caps 400 if not removed already, as the user may, for reduction or other reasons, remove the cap 400, manually or using a contemplated cap-removing tool (not shown), at any of various stages of the procedure.

Figure 15:
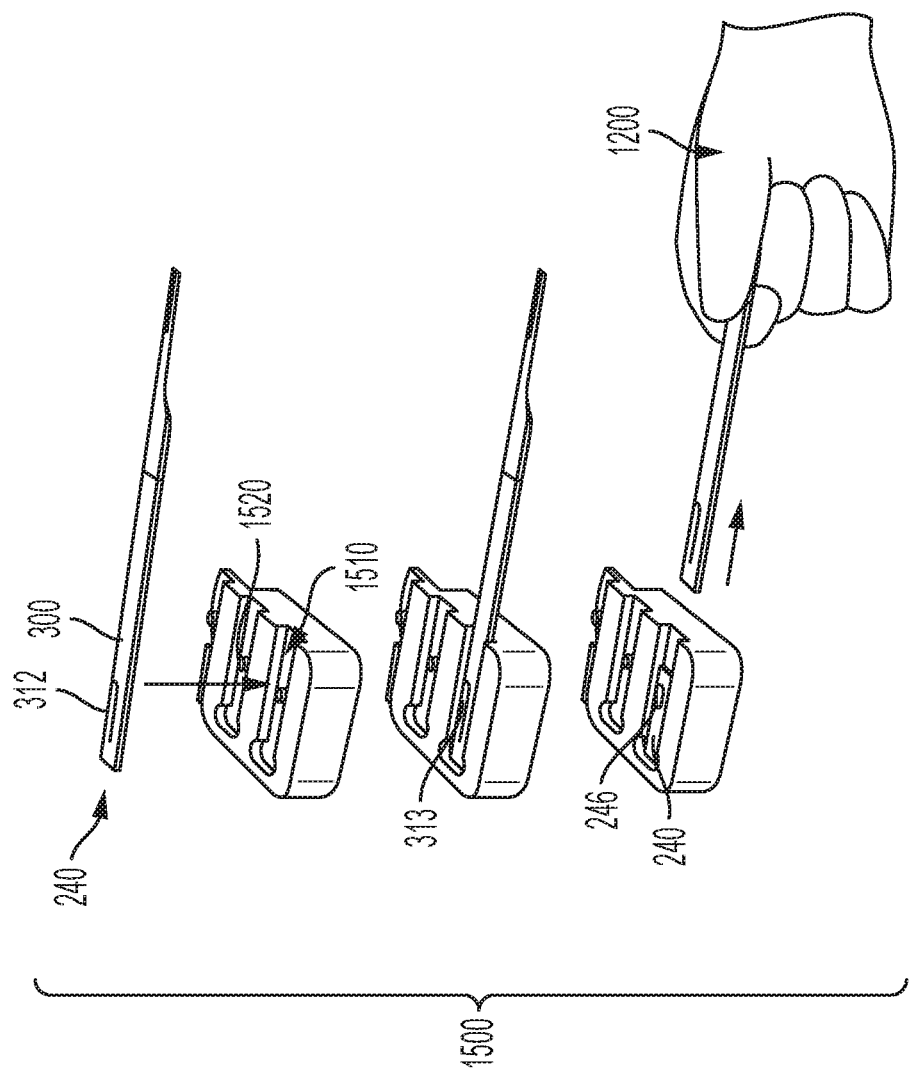
FIG. 15 shows in perspective view steps for removing the tab extenders from the extender tabs broken off with the extenders using a tab removing tool, according to embodiments of the present disclosure.

FIG. 15 shows in perspective view of post-procedures steps for removing, using a tab remover 1500, the tab extenders 300 from the extender tabs 240 broken off with the extenders 300 from the receiver 230. The tab remover 1500 can be referred to by other terms, such as break-off removal tool, extender remover, tab-extender remover, extender-tab remover, tab/extender separator, or the like.

To break-off the extender tabs, the user (e.g., surgeon or assistant) positions (e.g., slides) the tab remover 1500 over, or against, each of the tab extenders 300. Or, vice versa—the user positions the extenders 300 over the tab remover 1500.

The extenders 300 are positioned within an extender-receiving slot 1510 of the remover 1500. The slot 1510 includes a protrusion 1520 for engaging and pushing against the protrusion 313 of the locking component 312 of the tab extender 300. When the locking-component protrusion 313 is pushed up by the tab-remover protrusion 1520, the locking-component protrusion 313 is pushed out of engagement from the locking aperture 246 of the extender tab 240.

With the disengagement, the tab extender 300 can be easily slid or otherwise moved away from the extender tab 240, which remains at this stage intact with the tab remover 1500. The remover 1500 holds the tab 240 in place by engagement between the remover protrusion 1520 and the tab-locking aperture 246 of the extender tab 240. The tab 240 can then be retrieved from the remover 1500 and discarded or recycled.

Figure 16:
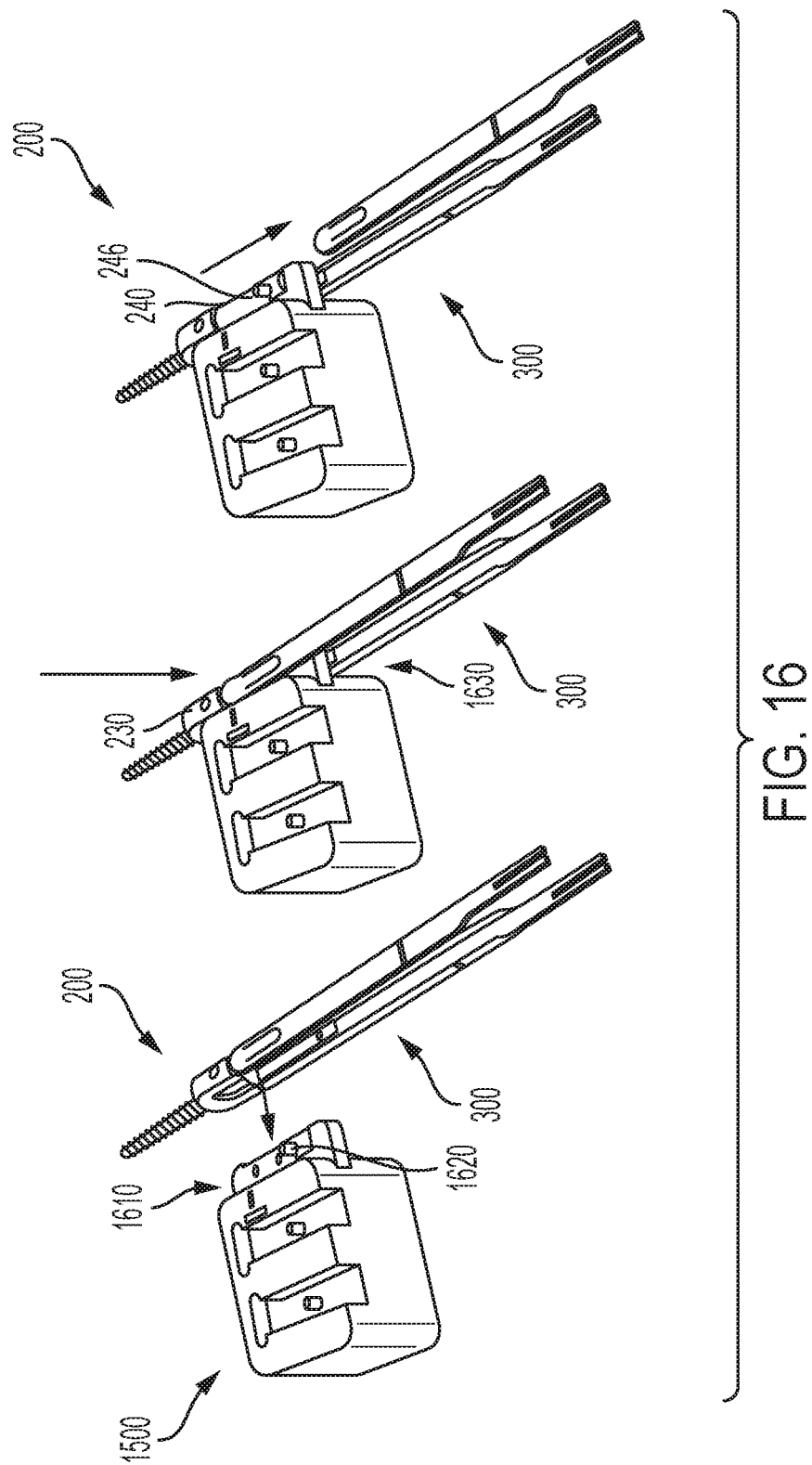
FIG. 16 shows in perspective view steps for using the tab remover to remove the extender tabs from the tab extenders, according to embodiments of the present disclosure.

In some cases, tab extenders 300 are attached to a screw assembly 200, including the extender tabs 240, but not implanted, and so not broken off from the extender tabs 240. A user may wish to detach the extenders 300 from the screw assembly 200. FIG. 16 shows in perspective view steps for using the tab remover 1500 to remove tab extenders 240 from extender tabs 230 still connected to the receiver 230. A user uses a second, end, slot 1610 having a protrusion 1620 for this, in a manner similar to how the user used the first remover slot 1510 and protrusion 1520.

The extender 300 is disengaged from the extender tab 240 by the slot protrusion 1620 pushing the extender protrusion 313 out of engagement with the locking aperture 246 of the extender tab 140. With the disengagement, the extender 300 can be easily slid away from the screw assembly 200, which remains for this step intact with the tab remover 1500, which holds the screw assembly 200 in place by engagement between the remover protrusion 1620 and the tab-locking aperture 246 of the screw assembly 200.

The remover 1500 in various embodiments includes a third slot 1630, opposite the second slot 1610. The slot 1630 can include a protrusion, like protrusion 1620, for engaging the opposite locking aperture 246 and extender protrusion. Both extenders can be removed in these embodiments without needing to flip the remover 1500 or system 100 components remaining intact.

In some embodiments, the remaining system components (screw assembly 200 and the second tab extender 300) are turned over for removing the second tab extender 300 using the slot 1610 and protrusion 1620.

Upon disengagement of the tab extenders 300 from the extender tabs 240, the non-used screw assembly 200 can be retrieved from the remover 1500 and, optionally, processed for sterilizing and use in a future procedure.

Figure 17:
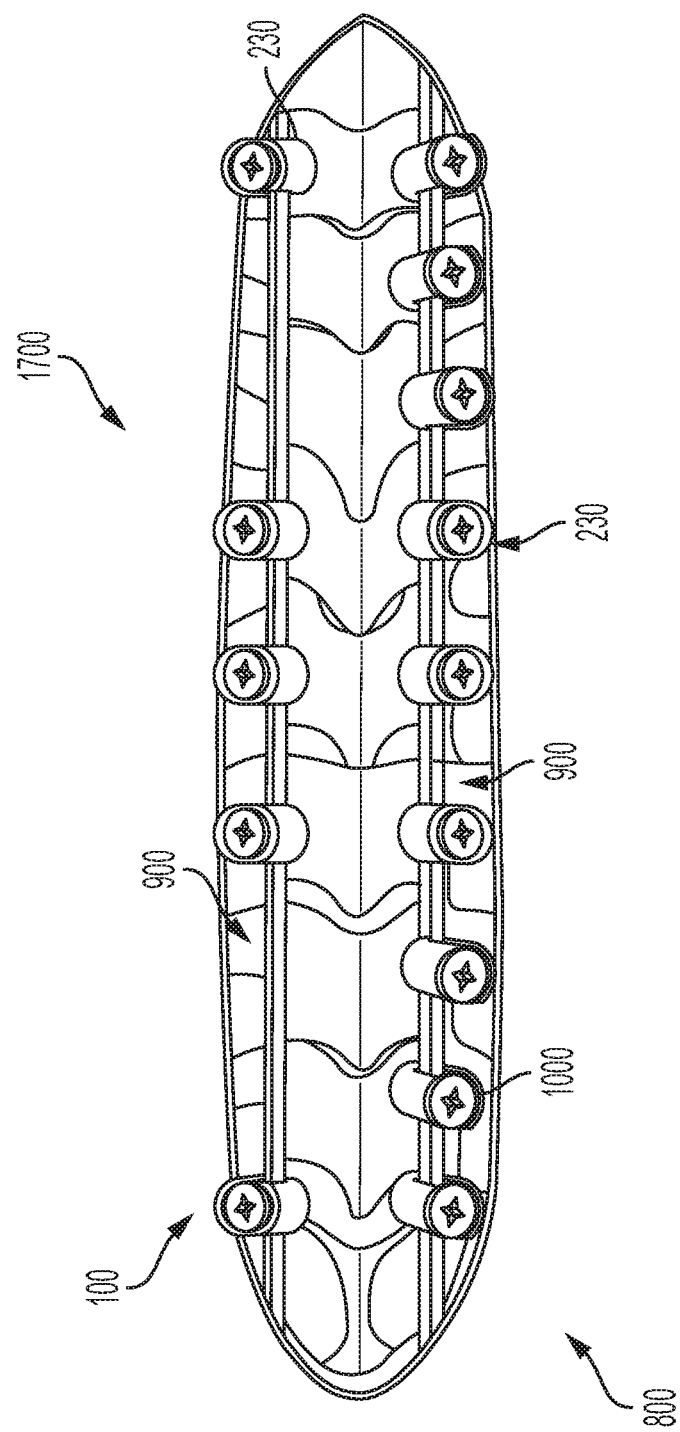
FIG. 17 is a plan view of the corrected spine, after the setscrews have been fully tightened and the capped extender tabs snapped off of the extended-tab screw implant.

FIG. 17 is a plan view of an example corrected spine, after finally tightening the setscrews 1000 and snapping off the towers—extender tabs 240, tab extenders 300, and any remaining caps 400—of the systems 100 from the receiver 230.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

In addition, while certain aspects of this disclosure are described as being performed by a single module or unit for purposes of clarity, it should be understood that the techniques of this disclosure may be performed by a combination of units or modules associated with a medical device, for example.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A system comprising:
    a spinal-correction system comprising:
        a receiver having a distal base and a pair of opposing arms extending proximally from the base forming a rod-receiving cavity,
        a pair of opposing first and second extender tabs having threaded inner walls sized and shaped for receiving threads of a setscrew, each extender tab being configured to be broken for separating from an associated arm at a breakoff section in operation of the spinal-correction system,
        a pair of first and second tab extenders, each being connectable releasably to a proximal end of one of the first and second extender tabs, and
        a cap instrument connectable releasably to an extender proximal end of the first and second tab extenders; and
    a removal tool including:
        a first slot configured to receive the first extender tab being broken-off and including a first projection to release the first tab extender from the first extender tab within the first slot, and
        a second slot configured to receive the second extender tab being broken-off and including a second projection to release the second tab extender from the second extender tab within the second slot, the first slot being adjacent to the second slot.

2. The system of claim 1, wherein a threadform of each inner wall of the first and second extender tabs extends from a distal end of each extender tab proximally least about half of a height of each extender tab.

3. The system of claim 1, wherein a threadform of each inner wall of the first and second extender tabs extends from a distal end of each extender tab proximally at least about two thirds of a height of each extender tab.

4. The system of claim 1, wherein:
    each extender tab comprises a locking aperture; and each tab extender comprises a locking protrusion for engagement with a corresponding one of the locking apertures to releasably engage the tab extender to the extender tab.

5. The system of claim 4, wherein:
each tab extender comprises a cantilever-spring locking component connected to a balance of the tab extender only at a distal end of the locking component; and
the locking protrusion is positioned at or adjacent a proximal end of the locking component.

6. The system of claim 1, wherein the cap instrument extends from a cap proximal end to a cap distal end and comprises cap inner walls extending from the cap proximal end to the cap distal end of the cap instrument, the cap inner walls defining:
a central-guide channel extending between the cap proximal and distal ends of the cap instrument; and
a tab-extender channel on each side of the central-guide channel.

7. The system of claim 6, wherein:
the cap instrument comprises:
an outer wall extending between the cap proximal and distal ends of the cap instrument; and
opposing engagement openings in each of the tab-extender channels, each of the engagement openings extending between and through the inner and outer walls of the cap instrument; and
each of the first and second tab extenders extends from the extender distal end to an extender proximal end having a forked tip comprising a pair of opposing prongs, at least one of the opposing prongs having a prong protrusion for, in use of the system, engaging with one of the engagement openings of the cap instrument.

8. The system of claim 7, wherein each of the prongs having one of the prong protrusions is configured to act as a cantilever spring biasing the prong protrusion outward, away from the opposing prong of the forked tip, thus forcing the prong protrusion into the engagement opening of the cap instrument when the forked tip is inserted in the tab-extender channel of the cap instrument.

9. The system of claim 1, wherein each tab extender comprises an inner wall and an outer wall, the inner wall at an extender distal end forming an extender-tab-receiving channel having a back wall, opposing side walls, and an internal shoulder wall extending from each side wall, the back wall, side walls, and shoulder walls forming a generally u-shaped extender-tab-receiving channel.

10. The system of claim 1, wherein the receiver is configured in a uni-axial format such that the receiver can be moved only along a single plane with respect to a bonescrew.

11. The system of claim 1, wherein the receiver is configured in a multi-axial format such that the receiver can be moved anywhere within a generally conical space with respect to a bonescrew.

12. A system comprising:
a spinal-correction system comprising:
a receiver having a distal base and a pair of opposing arms extending proximally from the base forming a rod-receiving cavity,
a pair of opposing first and second extender tabs having threaded inner walls sized and shaped for receiving threads of a setscrew, each extender tab configured to be broken for separation from an associated arm at a breakoff section, and
a pair of first and second tab extenders, each tab extender being connectable releasably to a corresponding extender tabs and the first and second tab extenders having a space therebetween; and
a removal tool having a first member and a second member joined along a side of the first member, the second member configured to be received in the space between the first and second tab extenders, the second member includes a projection to release the first extender tab from the first tab extender upon engagement with the first tab extender.

13. The system of claim 12, further comprising:
a cap instrument connectable releasably to an extender proximal end of the first and second tab extenders.

14. The system of claim 13, wherein:
each extender tab comprises a locking aperture; and
each tab extender comprises a locking protrusion for engagement with a corresponding one of the locking apertures to releasably engage the tab extender to the extender tab.

15. The system of claim 14, wherein:
each tab extender comprises a cantilever-spring locking component connected to a balance of each tab extender only at a distal end of the cantilever-spring locking component; and
the locking protrusion is positioned at or adjacent a proximal end of the cantilever-spring locking component.

16. The system of claim 13, wherein the cap instrument extends from a cap proximal end to a cap distal end and comprises inner walls extending from the cap proximal end to the cap distal end of the cap instrument, the inner walls defining:
a central-guide channel extending between the cap proximal and distal ends of the cap instrument; and
a tab-extender channel on each side of the central-guide channel.

17. The system of claim 12, wherein each tab extender comprises an inner wall and an outer wall, the inner wall at an extender distal end forming an extender-tab-receiving channel having a back wall, opposing side walls, and an internal shoulder wall extending from each side wall, the back wall, side walls, and shoulder walls forming a generally u-shaped extender-tab-receiving channel.

18. The system of claim 12, wherein the first member comprises:
a slot being configured to receive the first extender tab being broken-off and including a first projection to release the first tab extender from the first extender tab within the first slot.

19. The system of claim 18, wherein the slot is a first slot and the first member further comprises:
a second slot being configured to receive the second extender tab being broken-off and including a second projection to release the second tab extender from the second extender tab within the second slot, the first slot being adjacent to the second slot.

20. A system comprising:
a spinal-correction system comprising:
a receiver having a distal base and a pair of opposing arms extending proximally from the base forming a rod-receiving cavity,
a pair of opposing extender tabs having threaded inner walls sized and shaped for receiving threads of a setscrew, a threadform of each inner wall of the extender tabs extending from a distal end of the extender tab proximally at least about half of a total height of the extender tab, a pair of breakoff sections, each connecting one of the extender tabs to one of the receiver arms, and each being configured for being broken readily for separating the extender tab from the receiver arm in operation of the system, and a pair of first and second tab extenders, each being connectable releasably to a proximal end of one of the extender tab, the first and second tab extenders forming a space therebetween; and a removal tool including:

first projections configured to release the first and second extender tabs being broken-off from the first and second tab extenders, and second projections configured to, alternately, release the first and second extender tabs, coupled to the opposing arms, from the first and second tab extenders when the tool is in the space between the first and second tab extenders, wherein:

each extender tab comprises a locking aperture; and each tab extender comprises a locking protrusion for engagement with a corresponding one of the locking apertures to releasably engage the tab extender to the extender tab.

* * * * *